US007842802B2

(12) United States Patent
Scott et al.

(10) Patent No.: US 7,842,802 B2
(45) Date of Patent: *Nov. 30, 2010

(54) VINORELBINE DERIVATIVES

(75) Inventors: Ian L. Scott, Woodinville, WA (US);
Jeffrey M. Ralph, Niskayuna, NY (US);
Matthew E. Voss, Nassau, NY (US)

(73) Assignee: Albany Molecular Research, Inc.,
Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/331,691

(22) Filed: Dec. 10, 2008

(65) Prior Publication Data

US 2009/0088568 A1 Apr. 2, 2009

Related U.S. Application Data

(63) Continuation of application No. 11/931,080, filed on Oct. 31, 2007, now abandoned, which is a continuation of application No. 11/697,370, filed on Apr. 6, 2007, which is a continuation of application No. 11/003,583, filed on Dec. 3, 2004, now Pat. No. 7,235,564.

(60) Provisional application No. 60/527,194, filed on Dec. 4, 2003.

(51) Int. Cl.
C07D 487/00 (2006.01)
C07D 491/00 (2006.01)
C07D 513/00 (2006.01)
(52) U.S. Cl. .................................................... 540/476
(58) Field of Classification Search ........................ None
See application file for complete search history.

(56) References Cited

U.S. PATENT DOCUMENTS

| 4,307,100 | A | 12/1981 | Langlois et al. |
| 4,347,249 | A | 8/1982 | Potier et al. |
| 4,388,305 | A | 6/1983 | Trouet et al. |
| 4,430,269 | A | 2/1984 | Pearce |
| 4,639,456 | A | 1/1987 | Trouet et al. |
| 4,737,586 | A | 4/1988 | Potier et al. |
| 4,769,453 | A | 9/1988 | Potier et al. |
| 5,047,528 | A | 9/1991 | Kutney et al. |
| 6,127,377 | A | 10/2000 | Duflos et al. |
| RE37,449 | E | 11/2001 | Kutney et al. |
| 6,365,735 | B1 | 4/2002 | Rool |
| 7,235,564 | B2 | 6/2007 | Scott et al. |
| 7,238,704 | B2 | 7/2007 | Scott et al. |
| 2004/0186286 | A1 | 9/2004 | Fukuyama et al. |
| 2005/0137169 | A1 | 6/2005 | Scott et al. |
| 2007/0179170 | A1 | 8/2007 | Scott et al. |
| 2007/0179171 | A1 | 8/2007 | Scott et al. |
| 2008/0051425 | A1 | 2/2008 | Scott et al. |
| 2008/0108644 | A1 | 5/2008 | Scott et al. |
| 2008/0119502 | A1 | 5/2008 | Wolf et al. |
| 2008/0125451 | A1 | 5/2008 | Wolf et al. |

FOREIGN PATENT DOCUMENTS

| CA | 2458600 | | 3/2003 |
| CN | 101108859 | A | 1/2008 |
| EP | 0292463 | A2 | 11/1988 |
| EP | 1426377 | A1 | 6/2004 |
| FR | 2707988 | A1 | 1/1995 |
| JP | 2003064084 | | 3/2003 |
| WO | 8605491 | A1 | 9/1986 |
| WO | 2005055939 | A2 | 6/2005 |
| WO | 2005055943 | A2 | 6/2005 |
| WO | 2008/011805 | A1 | 1/2008 |
| WO | 2008/033935 | A2 | 3/2008 |
| WO | 2008033930 | A2 | 3/2008 |

OTHER PUBLICATIONS

Barthe et al., "Optimization of the Separation of Vinca Alkaloids by Nonaqueous Capillary Electrophoresis," Journal of Chromatography A 968:241-50 (2002).
International Search Report for International Patent Application No. PCT/US07/78281 (Sep. 3, 2008).
Sheng et al., "Synthesis and Biological Evaluation of C-12' Substituted Vinflunine Derivatives," Shanghai Hengrui Pharmaceutical Co. Ltd. Shanghai China, Poster Presented at 235th ACS National Meeting, New Orleans, LA (Apr. 6-10, 2008).
Supplementary European Search Report for European Patent Application No. EP04813161 (May 13, 2009).
Yamaguchi et al., "Identification of Novel Metabolites of Vinorelbine in Rat," Xenobiotica 28(3):281-91 (1998) Abstract.
Berge et al., "Pharmaceutical Salts," Journal of Pharmaceutical Sciences 66(1):1-19 (1997).
Boyd, M.R., "Anticancer Drug Development Guide: Preclinical Screening, Clinical Trials, and Approval," Teicher, B. Ed., Humana Press, Totowa, New Jersey, pp. 23-42 (1997).
Skehan et al., "New Colorimetric Cytotoxicity Assay for Anticancer-Drug Screening," Journal of the National Cancer Institute 82(13):1107-1112 (1990).
Fahy, J., "Modifications in the << upper >> or Velbenamine Part of the Vinca Alkaloids Have Major Implications for Tubulin Interacting Activities," Current Pharmaceutical Design 7:1181-1197 (2001).
Lobert et al., "Vinca Alkaloid-Induces Tubulin Spiral Formation Correlates with Cytotoxicity in the Leukemic L 1210 Cell Line," Biochemistry 39:12053-12062 (2000).
Ram & Kumari, "Natural Products of Plant Origin as Anticancer Agents," Drug News Perspect 14(8):465-482 (2001).
CAS(R) Registry No. 81600-06-8, 1985.
CAS(R) Registry No. 123286-01-1; 123286-00-0, 1991.
CAS(R) Registry No. 67699-41-6; 67699-40-5, 1984.
Anhydrovinblastine, Pioneer, IMSworld Publications Ltd (2000) (Update Date May 8, 2000).
Vinxaltine; S 12363, Pioneer, IMSworld Publications Ltd (2000) (Update Date May 22, 1995).
Vinflunine; F 12158; L 0070, Pioneer, IMSworld Publications Ltd (2000) (Update Date Apr. 19, 1999).

(Continued)

*Primary Examiner*—James O Wilson
*Assistant Examiner*—Noble Jarrell
(74) *Attorney, Agent, or Firm*—Nixon Peabody LLP

(57) ABSTRACT

The present invention relates to novel vinorelbine derivatives. Pharmaceutical compositions containing these compounds as well as processes of preparation and processes of use for treatment of various conditions are also disclosed.

3 Claims, No Drawings

OTHER PUBLICATIONS

Napavin, Pioneer, IMSworld Publications Ltd (2000) (Update Date Oct. 25, 1999).
Registry No. 166533-14-8, SciFinder (Feb. 28, 2002).
Registry No. 105801-71-6, SciFinder (Feb. 28, 2002).
Registry No. 105801-70-5, SciFinder (Feb. 28, 2002).
Registry No. 108893-99-8, SciFinder (Feb. 28, 2002).
Registry No. 108893-98-7, SciFinder (Feb. 28, 2002).
Registry No. 218128-76-8, SciFinder (Feb. 28, 2002).
Registry No. 54112-69-5, SciFinder (Feb. 28, 2002).
Registry No. 108893-97-6, SciFinder (Feb. 28, 2002).
Registry No. 108893-96-5, SciFinder (Feb. 28, 2002).
Registry No. 90012-98-9, SciFinder (Feb. 28, 2002).
Registry No. 90012-97-8, SciFinder (Feb. 28, 2002).
Mangeney et al., "A New Class of Antitumor Compounds: 5'-Nor and 5',6'-Seco Derivatives of Vinblastine-Type Alkaloids," Journal of Organic Chemistry, 44(22):3765-68 (1979).
Bau et al., "Crystal Structure of Vinblastine," J. Chem. Soc. Perkin Trans. pp. 2079-2082 (2000).
Cros et al., "Experimental Antitumor Activity of Navelbine," Seminars in Oncology 16(2)(Suppl. 4):15-20 (1989).
Keuhne et al., "Syntheses and Biological Evaluation of Vinblastine Congeners," Organic and Biomolecular Chemistry 1:2120-36 (2003).
Lavoie et al., "Bioisosterism: A Rational Approach in Drug Design," Chemical Reviews 96:3147-76 (1996).
Merck Index, "Vindesine," 9982, 9986, 9987, and 9989, 2006.
Moncrief et al., "Structures of Leurocristine (Vincristine) and Vincaleukoblastine X-Ray Analysis of Leurocristine Methiodide," Journal of American Chemical Society 87(21):4963-4964 (1965).
Neuss et al., "Vinca Alkaloids XXXIII[1]. Microbiological Conversions of Vincaleukoblastine (VLB, Vinblastine), an Antitumor Alkaloid from Vinca rosea," Helvetica Chimica Acta 57(6):1886-90 (1974).
Sheng et al., "Synthesis and Biological Evaluation of C-12' Substituted Vinflunine Derivatives," Bioorganic & Medicinal Chemistry Letters 18:4602-4605 (2008).
Voss et al., "Synthesis and SAR of Vinca Alkaloid Analogues," Bioorganic & Medicinal Chemistry Letters 19:1245-1249 (2009).

VINORELBINE DERIVATIVES

This application is a continuation of U.S. patent application Ser. No. 11/931,080, filed Oct. 31, 2007, which is a continuation of U.S. patent application Ser. No. 11/697,370, filed Apr. 6, 2007, which is a continuation of U.S. patent application Ser. No. 11/003,583, filed Dec. 3, 2004, now U.S. Pat. No. 7,235,564, which claims benefit of U.S. Provisional Patent Application Ser. No. 60/527,194, filed Dec. 4, 2003, which are hereby incorporated by reference in their entirety.

FIELD OF THE INVENTION

The present invention relates to vinorelbine derivatives which are potent inhibitors of cellular mitosis and proliferation, as well as pharmaceutical compositions, preparation processes, and methods of use for treatment of various conditions.

BACKGROUND OF THE INVENTION

Cellular Proliferation and Cancer

The disruption of external or internal regulation of cellular growth can lead to uncontrolled cellular proliferation and in cancer, tumor formation. This loss of cellular growth control can occur at many levels and, indeed, does occur at multiple levels in most tumors. Under these circumstances, although tumor cells can no longer control their own proliferation, such cells still must use the same basic cellular machinery employed by normal cells to drive their growth and replication.

Mitosis and Spindle Formation

In a process known as mitosis, cancer cells, like all mammalian cells, multiply through replication and segregation of the original chromosomes. Following DNA replication in the S phase, the cells progress in the G2 phase. During the G2 phase, cells continue to increase in mass and prepare for mitosis. If chromosome damage is present in the G2 phase, the affected cell responds by activating the G2 phase checkpoint, which prevents progression into mitosis. In the absence of DNA damage or following repair of damage, the G2 phase cells then enter the M phase in which the identical pairs of chromosomes are separated and transported to opposite ends of the cell. The cell then undergoes division into two identical daughter cells.

In a process known as spindle formation, the cell utilizes the mitotic spindle apparatus to separate and pull apart the chromosomes. This apparatus, in part, consists of a network of microtubules that form during the first stage of mitosis. Microtubules are hollow tubes that are formed by the assembly of tubulin heterodimers from alpha- and beta-tubulin. The assembly of tubulin into microtubules is a dynamic process with tubulin molecules being constantly added and subtracted from each end.

Vinca Compounds as Inhibitors of Mitosis and Cellular Proliferation

In general, vinca compounds are known to be inhibitors of mitosis and cellular proliferation. In particular, the antiproliferative activity of the vinca alkaloid class of drugs has been shown to be due to their ability to bind tubulin. Assembly of tubulin into microtubules is essential for mitosis and the binding of the vincas to tubulin leads to cell cycle arrest in M phase and subsequently to apoptosis. For example, at low concentrations, these compounds interfere with the dynamics of microtubule formation. At higher concentrations, they cause microtubule disassembly, and at still higher concentrations, the formation of tubulin paracrystals.

Moreover, the anti-cancer activity of vinca alkaloids is generally believed to result from a disruption of microtubules resulting in mitotic arrest. However, cytotoxicity of vinca alkaloids also has been demonstrated in non-mitotic cells. Considering the role of microtubules in many cellular processes, the cytotoxic action of vinca alkaloids may involve contributions from inhibition of non-mitotic microtubule-dependent processes.

Cytotoxicity may also be a consequence of changes in membrane structure resulting from the partitioning of vinca alkaloids into the lipid bilayer. Studies with another tubulin binding compound, taxol, have shown that cell cycle arrest was not a precondition for apoptosis by agents of this type. Therefore, the anti-cancer activity of vinca alkaloids may be the result from disruption of a number of distinct microtubule-dependent and possibly microtubule-independent processes.

The assembly of tubulin into microtubules is a complex process involving dynamic instability (i.e. the switching between periods of slow growth and rapid shortening at both ends of the microtubule), and treadmilling (i.e. the addition of tubulin to one end of the microtubule occurring at the same rate as loss of tubulin from the other). Low concentrations of vinca alkaloids have been shown to bind to the ends of the microtubules and suppress both microtubule instability and treadmilling during the metaphase stage of mitosis. For example, vinca alkaloids have been shown to stabilize microtubule plus ends and destabilize microtubule minus ends. Although the spindle is retained under these conditions, there is frequently abnormal alignment of condensed chromosomes. At higher concentrations of vinca alkaloids, the spindle is not present and the chromosome distribution resembles that of prometaphase cells. At both low and high concentrations of vincas, mitotic arrest results from activation of metaphase-anaphase checkpoint. The molecular basis of this checkpoint is a negative signal sent from the kinetochore of chromosomes that are not attached to microtubules. This signal prevents the activation of pathways that result in the initiation of anaphase events.

Although there is a common binding site for the vinca alkaloids on tubulin, the members of this class do behave differently. The relative overall affinities for β-tubulin binding are vincristine>vinblastine>vinorelbine>vinflunine, but there is no significant difference in the affinity of all four drugs for tubulin heterodimers. The discrepancy has primarily been explained by differences in the affinities of vinca-bound heterodimers for spiral polymers and the binding of drug to unliganded polymers. For example, tubulin spirals induced by vinflunine are significantly smaller than those induced by vinorelbine.

In addition, vinca alkaloids also differ in their effects on microtubule dynamics. Vinflunine and vinorelbine suppress dynamic instability through: slowing the microtubule growth rate, increasing the mean duration of a growth event and reducing the duration of shortening. In contrast, vinblastine reduces the rate of shortening and increases the percentage of time the microtubules spend in the attenuated state. Vinblastine, vinorelbine, and vinflunine all suppress treadmilling, with vinblastine displaying the greatest potency.

In Vivo Properties

The vinca derivatives fall into the general class of cytotoxic anti-cancer agents and, as such, suffer from the same problem as all cytotoxics—i.e., toxicity. Vincristine and vinblastine are neurotoxic. Vinorelbine, which is structurally very similar to vinblastine and vincristine and is only slightly less potent, is less neurotoxic. This change in toxicity cannot be explained by examination of the binding affinity of these compounds for tubulin alone. It has been postulated to arise from an increase in sensitivity to changes in microtubule dynamics in tumor cells and, as described above, these compounds have been shown to have subtly different effects. It could also arise from changes in cellular uptake of the drug. Vinflunine is not very potent in vitro yet is active in vivo, and this has been attributed to its superior cellular uptake. There are also quite significant differences in the profile of efficacy of vinca alkaloids. Vincristine has found wide use in the treatment of hematologic malignancies including leukemias and lymphomas. It is also widely used in pediatric solid tumors and, in the past, in small cell lung cancer. Vinblastine is an important component of the combination regimen that is curative for testicular cancer. Vinorelbine is quite different and has found use mainly in breast cancer and non-small cell lung cancer.

There remains a need for novel vinca derivatives with improved pharmacological and therapeutic properties, improved processes for the preparations of such vinca derivative compounds, corresponding pharmaceutical compositions, and methods of use.

The present invention is directed to achieving these objectives.

SUMMARY OF THE INVENTION

The present invention relates to a compound of Formula (I) as follows:

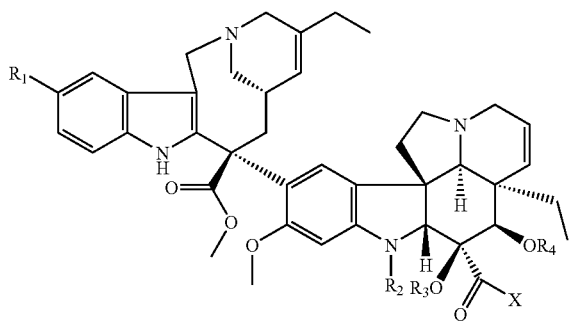

Formula I where:

$R_1$=alkyl;
alkenyl;
alkynyl;
aryl;
heterocyclyl;
halogen;
CN;
CH(O);
$COR_5$;
$SO_2NHNH_2$;
$SO_2NR_5NH_2$;
$SO_2NR_5NHR_6$;
$SO_2NR_5NR_6R_7$;
$SO_2NHNHR_5$;
$SO_2NHNR_5R_6$;
$CO_2R_5$;
$SR_5$;
$SSR_5$;
$SOR_5$;
$SO_2R_5$;
$SO_2NHR_5$;
$SO_2NR_5R_6$;
$B(OR_5)_2$;
$CF_3$;
SH;
$SO_2NH_2$;
$NH_2$;
$NHR_5$;
$NHCOR_5$;
$NHSO_2R_5$;
$NR_5R_6$;
$NR_5COR_6$; or
$NR_5SO_2R_6$;
$R_5$ and $R_6$ can form a ring $R_2$=alkyl or CH(O);

$R_3$=hydrogen, alkyl, or $C(O)R_5$;

$R_4$=hydrogen or $C(O)R_5$;

$R_5$ and $R_6$ each are independently alkyl, alkenyl, alkynyl, aryl, or heterocyclyl;

$X=OR_5$, $NR_5R_6$, $NHNH_2$, $NHNHC(O)R_5$, OH, $NHR_5$, $NH_2$, or NHNHC(O)H;

$R_4$ and X may be linked together with intervening atoms to form a ring; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

Most preferably:

$R_1$=alkyl;
alkenyl;
alkynyl;
aryl;
heterocyclyl;
halogen;
CN;
CH(O);
$COR_5$;
$CO_2R_5$;
$SR_5$;
$SSR_5$;
SH;
$NH_2$;
$NHR_5$; or
$NR_5R_6$;

More preferably:

$R_1$=alkyl;
alkenyl;
alkynyl;
halogen;
CN;
$SR_5$;
$SSR_5$;
SH;
$NH_2$;
$NHR_5$;
$NR_5R_6$; where $R_5$ and $R_6$ form a ring Another aspect of the present invention relates to a process for preparation of a derivative product compound of Formula (I) as follows:

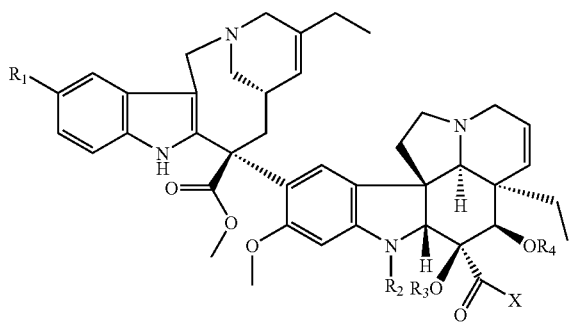

Formula I where:

R$_1$ is:
  alkyl;
  alkenyl;
  alkynyl;
  aryl;
  heterocyclyl;
  CN;
  CH(O);
  COR$_5$;
  SO$_2$NHNH$_2$;
  SO$_2$NR$_5$NH$_2$;
  SO$_2$NR$_5$NHR$_6$;
  SO$_2$NR$_5$NR$_6$R$_7$;
  SO$_2$NHNHR$_5$;
  SO$_2$NHNR$_5$R$_6$;
  CO$_2$R$_5$;
  SR$_5$;
  SSR$_5$;
  SOR$_5$;
  SO$_2$R$_5$;
  SO$_2$NHR$_5$;
  SO$_2$NR$_5$R$_6$;
  B(OR$_5$)$_2$;
  CF$_3$;
  SH;
  SO$_2$NH$_2$;
  NH$_2$;
  NHR$_5$;
  NHCOR$_5$;
  NHSO$_2$R$_5$;
  NR$_5$R$_6$;
  NR$_5$COR$_6$; or
  NR$_5$SO$_2$R$_6$;
  R$_5$ and R$_6$ can form a ring;

R$_2$=alkyl or CH(O);

R$_3$=hydrogen, alkyl, or C(O)R$_5$;

R$_4$=hydrogen or C(O)R$_5$;

R$_5$ and R$_6$ each are independently alkyl, alkenyl, alkynyl, aryl, or heterocyclyl;

X=OR$_5$, NR$_5$R$_6$, NHNH$_2$, NHNHC(O)R$_5$, OH, NHR$_5$, NH$_2$, or NHNHC(O)H;

R$_4$ and X may be linked together with intervening atoms to form a ring; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted. The process involves converting an intermediate compound of formula:

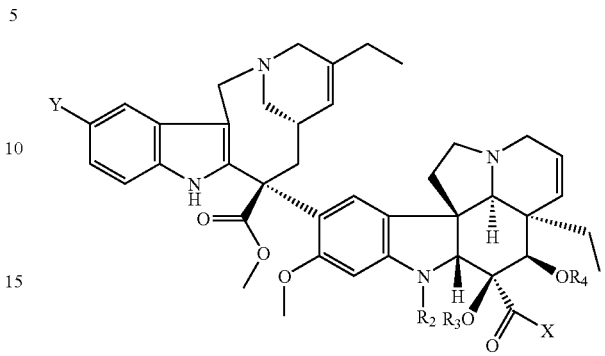

wherein Y is a halogen, under conditions effective to produce the product compound of Formula (I).

Another aspect of the present invention relates to a process for preparation of a derivative product compound of Formula (I) as follows:

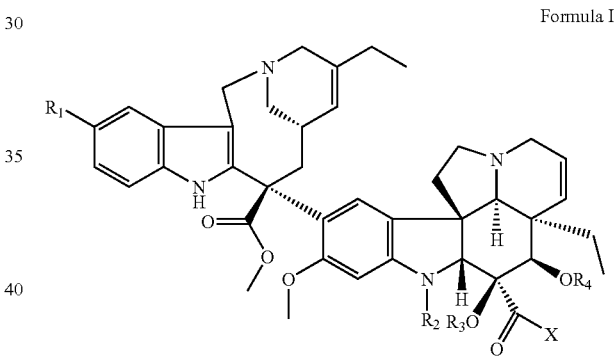

Formula I where:

R$_1$ is:
  halogen;

R$_2$=alkyl or CH(O);

R$_3$=hydrogen, alkyl, or C(O)R$_5$;

R$_4$=hydrogen or C(O)R$_5$;

R$_5$ and R$_6$ each are independently alkyl, alkenyl, alkynyl, aryl, or heterocyclyl;

X=OR$_5$, NR$_5$R$_6$, NHNH$_2$, NHNHC(O)R$_5$, OH, NHR$_5$, NH$_2$, or NHNHC(O)H;

R$_4$ and X may be linked together with intervening atoms to form a ring; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted. The process involves halogenating a starting material of the formula:

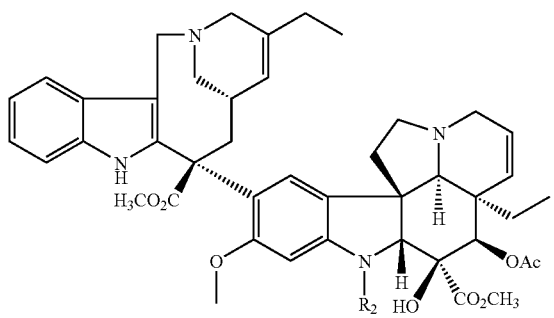

under conditions effective to form the derivative product compound.

The present invention also relates to a method for inhibiting cell proliferation in mammals, which comprises administering a therapeutically effective amount of the compound of Formula (I) to the mammal.

The present invention also relates to a method for treating a condition in mammals, which comprises administering a therapeutically effective amount of the compound of Formula (I) to the mammal. The condition can be bacterial infection, allergy, heart disease, AIDS, Human T-lymphotropic virus 1 infection, Human herpesvirus 3, Human herpesvirus 4, Human papillomavirus, diabetes mellitus, rheumatoid arthritis, Alzheimer's Disease, inflammation, arthritis, asthma, malaria, autoimmune disease, eczema, Lupus erythematosus, psoriasis, rheumatic diseases, Sjogren's syndrome, and viral infection.

The present invention also relates to a pharmaceutical composition of matter, which comprises the compound of Formula (I) and one or more pharmaceutical excipients.

DETAILED DESCRIPTION OF THE INVENTION

The present invention relates to novel vinorelbine derivatives, corresponding pharmaceutical compositions, preparation processes, and methods of use for treatment of various conditions.

In general, the novel compounds of the vinca family of compounds of the present invention, include derivatives of vinorelbine. In accordance with the present invention, such derivative compounds are represented by the chemical structures of Formula (I) as shown herein.

In particular, the present invention relates to a compound of Formula (I) as follows:

Formula I

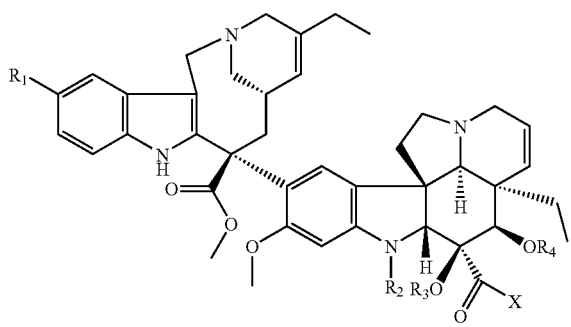

where:

$R_1$ is:
  alkyl;
  alkenyl;
  alkynyl;
  aryl;
  heterocyclyl;
  halogen;
  CN;
  CH(O);
  $COR_5$;
  $SO_2NHNH_2$;
  $SO_2NR_5NH_2$;
  $SO_2NR_5NHR_6$;
  $SO_2NR_5NR_6R_7$;
  $SO_2NHNHR_5$;
  $SO_2NHNR_5R_6$;
  $CO_2R_5$;
  $SR_5$;
  $SSR_5$;
  $SOR_5$;
  $SO_2R_5$;
  $SO_2NHR_5$;
  $SO_2NR_5R_6$;
  $B(OR_5)_2$;
  $CF_3$;
  SH;
  $SO_2NH_2$;
  $NH_2$;
  $NHR_5$;
  $NHCOR_5$;
  $NHSO_2R_5$;
  $NR_5R_6$;
  $NR_5COR_6$; or
  $NR_5SO_2R_6$;
  $R_5$ and $R_6$ can form a ring;

$R_2$=alkyl or CH(O);

$R_3$=hydrogen, alkyl, or $C(O)R_5$;

$R_4$=hydrogen or $C(O)R_5$;

$R_5$ and $R_6$ each are independently alkyl, alkenyl, alkynyl, aryl, or heterocyclyl;

X=$OR_5$, $NR_5R_6$, $NHNH_2$, $NHNHC(O)R_5$, OH, $NHR_5$, $NH_2$, or NHNHC(O)H;

$R_4$ and X may be linked together with intervening atoms to form a ring; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

In one embodiment, the present invention relates to a compound where $R_3$=acetyl.

In another embodiment, the present invention relates to a compound where $R_4$ hydrogen.

In another embodiment, the present invention relates to a compound where X=OMe.

In another embodiment, the present invention relates to a compound where $R_3$=acetyl, $R_4$=hydrogen, and X=OMe.

In another embodiment, the present invention relates to a compound where $R_2$=CH(O).

In another embodiment, the present invention relates to a compound where $R_2$=alkyl.

Representative examples of the compounds of Formula (I) are set forth in Table 1 below:
TABLE 1
Compounds of Formula (I)
| Example Number | COMPOUND OF FORMULA (I) | NAME OF VINCA COMPOUND |
|---|---|---|
| 1 | 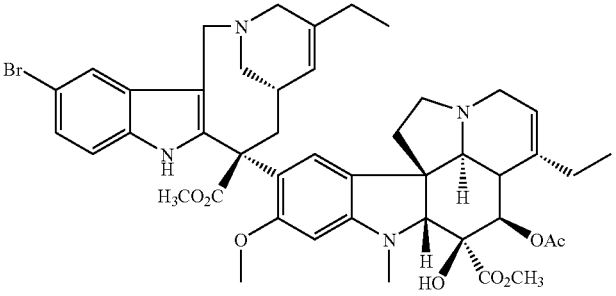 | 11'-bromovinorelbine |
| 2 | 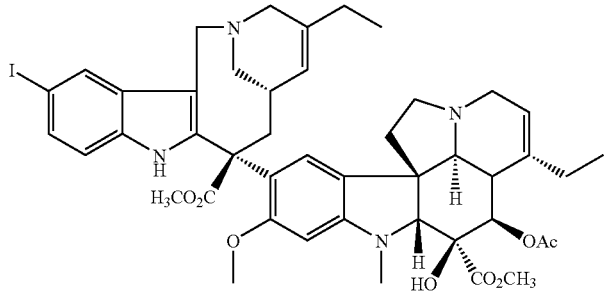 | 11'-iodovinorelbine |
| 3 | 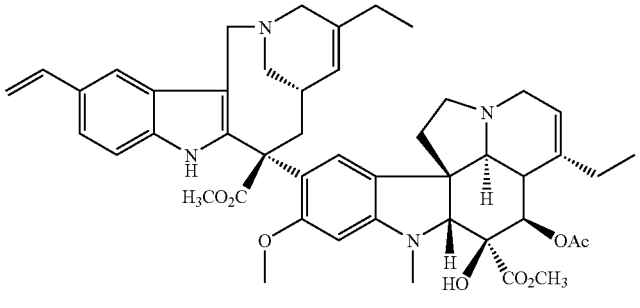 | 11'-vinylvinorelbine |
| 4 | 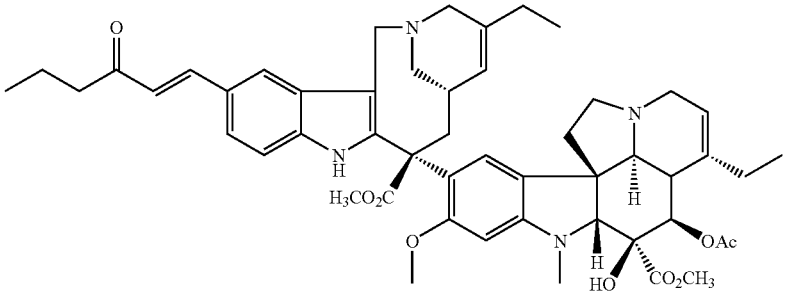 | 11'-(3-oxohex-1-enyl) vinorelbine |

TABLE 1-continued

Compounds of Formula (I)

| Example Number | COMPOUND OF FORMULA (I) | NAME OF VINCA COMPOUND |
|---|---|---|
| 5 | | 11'-(2-tert-butoxy carbonylvinyl) vinorelbine |
| 6 | | 11'-(carboxyvinyl) vinorelbine |
| 7 | | 11'-(methoxycarbonyl ethylsulfanyl) vinorelbine |
| 8 | | 11'-thiovinorelbine |

TABLE 1-continued

Compounds of Formula (I)

| Example Number | COMPOUND OF FORMULA (I) | NAME OF VINCA COMPOUND |
|---|---|---|
| 9 | | 11'-(methoxycarbonyl methylsulfanyl) vinorelbine |
| 10 | | 11'-(methylsulfanyl) vinorelbine |
| 11 | | 11'-(ethylsulfanyl) vinorelbine |
| 12 | | 11'-(4-hydroxybutyl sulfanyl)vinorelbine |
| 13 | | 11'-(3-hydroxypropyl sulfanyl)vinorelbine |

TABLE 1-continued

Compounds of Formula (I)

| Example Number | COMPOUND OF FORMULA (I) | NAME OF VINCA COMPOUND |
|---|---|---|
| 14 | | 11'-(2-hydroxyethyl sulfanyl)vinorelbine |
| 15 | | 11'-(2-fluorobenzyl sulfanyl)vinorelbine |
| 16 | | 11'-(2-chlorobenzyl sulfanyl)vinorelbine |
| 17 | | 11'-(phenylsulfanyl) vinorelbine |

TABLE 1-continued

Compounds of Formula (I)

| Example Number | COMPOUND OF FORMULA (I) | NAME OF VINCA COMPOUND |
|---|---|---|
| 18 | | 11'-(3-hydroxyphenylsulfanyl)vinorelbine |
| 19 | | 11'-(3-hydroxyethylsulfinyl)vinorelbine |
| 20 | | 11'-(3-hydroxypropylsulfinyl)vinorelbine |
| 21 | | 11'-ethynylvinorelbine |

TABLE 1-continued
Compounds of Formula (I)
| Example Number | COMPOUND OF FORMULA (I) | NAME OF VINCA COMPOUND |
|---|---|---|
| 22 | 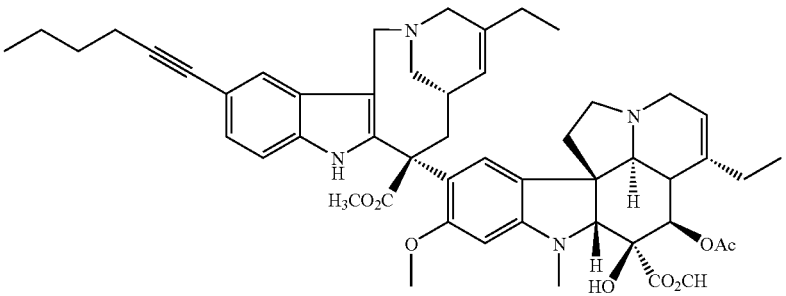 | 11'-hexynylvinorelbine |
| 23 | 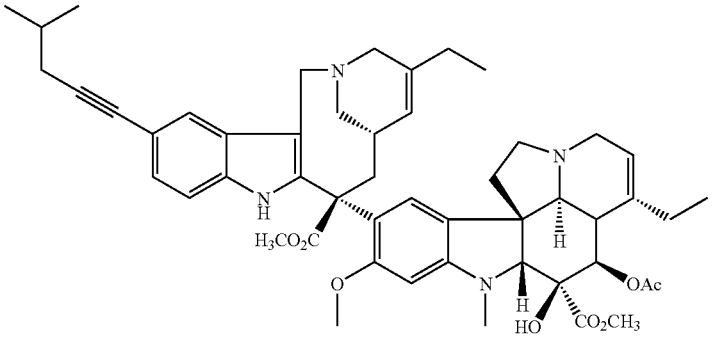 | 11'-(4-methylpentynyl) vinorelbine |
| 24 | 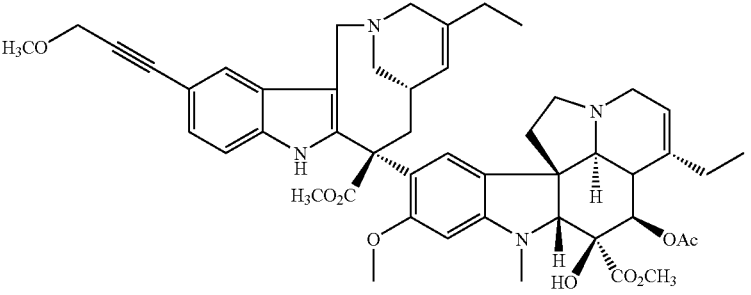 | 11'-(3-methoxy propynyl)vinorelbine |
| 25 | 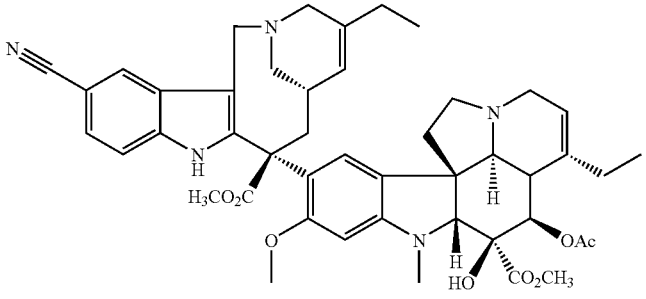 | 11'-cyanovinorelbine |

TABLE 1-continued

Compounds of Formula (I)

| Example Number | COMPOUND OF FORMULA (I) | NAME OF VINCA COMPOUND |
|---|---|---|
| 26 | | 11'-acetylvinorelbine |
| 27 | | 11'-(methoxycarbonyl)vinorelbine |
| 28 | | 11'-(2,2,2-trichloroethoxycarbonyl)vinorelbine |
| 29 | | 11'-(2,2-dichloroethoxycarbonyl)vinorelbine |
| 30 | | 11'-phenylvinorelbine |

TABLE 1-continued

Compounds of Formula (I)

| Example Number | COMPOUND OF FORMULA (I) | NAME OF VINCA COMPOUND |
|---|---|---|
| 31 | | 11'-(3-hydroxyphenyl) vinorelbine |
| 32 | | 11'-(3,5-dimethyl isoxazol-4yl)vinorelbine |
| 33 | | 3,11'-dimethyl vinorelbine |
| 34 | | 3-methyl-11'-iodo vinorelbine |
| 35 | | 11'-aminovinorelbine |

TABLE 1-continued

Compounds of Formula (I)

| Example Number | COMPOUND OF FORMULA (I) | NAME OF VINCA COMPOUND |
|---|---|---|
| 36 | | 11'-(4-methoxyphenyl amino)vinorelbine |

In yet another embodiment of the present invention, a complex can be formed which includes 2 structures of Formula (I) joined together at their $R_1$ groups, wherein each $R_1$ is —S—.

The synthetic reaction schemes for the preparation of compounds of Formula (I) are depicted below.

A synthetic scheme for preparing compounds of Formula (I) is shown in Scheme 1 below. A vinca alkaloid is treated with either N-iodosuccinimide to introduce an iodine in the 11'-position or subjected to enzymatic bromination to introduce a bromine in the 11'-position. Pd-mediated coupling is then used to introduce other functionality at this position. This methodology can be used to introduce alkyl, alkenyl, alkynyl, aryl, heterocyclyl, acyl and formyl groups and to form sulphides. Each of these groups can then be subjected to further derivitization following stand methods of organic synthesis.

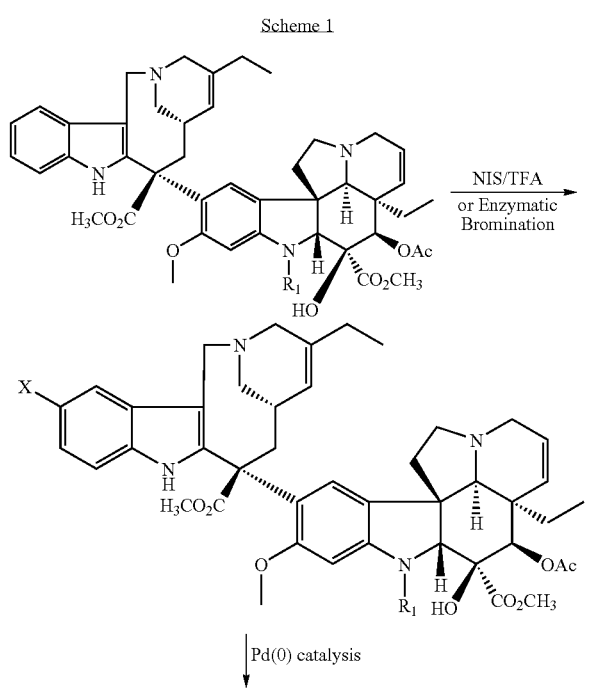

Scheme 1

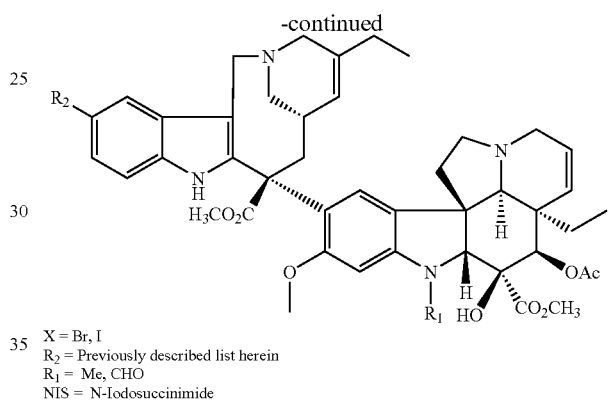

X = Br, I
$R_2$ = Previously described list herein
$R_1$ = Me, CHO
NIS = N-Iodosuccinimide In practicing either of the above processes, a variety of catalysts may be utilized, such as palladium chloride, palladium acetate, tetrakis(triphenylphosphine) palladium(0), tris(dibenzylideneacetone)dipalladium(0), dichlorobis(triphenylphosphine) palladium(II), benzylchlorobis(triphenylphosphine)palladium(II), [1,1'-bis(diphenylphosphino)ferrocene]dichloropalladium(II), tetrakis(triphenylphosphine)palladium, or bis(triphenylphosphine) palladium(II)dichloride. Additionally, the catalyst reactivity can be modified by addition of appropriate ligands or additives. Representative ligands or additives include: 2-(dicyclohexylphosphino)-2',4',6'-tri-1-propyl-1,1'-biphenyl, 2-(dicyclohexylphosphino)-2',6'-dimethoxy-1,1'-biphenyl, $PPh_3$, t-$Bu_3$P, CuI, or CuBr.

Based on the results obtained in the standard pharmacological test procedures described below, the compounds of the present invention are useful in inhibiting cellular proliferation in a mammal by administering to such mammal an effective amount of compound(s) of the present invention.

In particular, such vinca derivatives are useful as antineoplastic agents. More particularly, the compounds of the present invention are useful for inhibiting the growth of neoplastic cells, causing cell death of neoplastic cells, and eradicating neoplastic cells. The compounds of the present invention are, therefore, useful for treating solid tumors, (e.g., sarcomas), carcinomas, (e.g., astrocytomas), lymphomas, (e.g., adult T-cell lymphoma), different cancer disease types, (e.g., prostate cancer, breast cancer, small cell lung cancer, ovarian cancer, (Hodgkin's Disease), and other neoplastic disease states (e.g., leukemias, particularly adult T-cell leukemias).

Since vinca compounds are known to be tubulin inhibitors, the compounds of the present invention would also be expected to be useful in treating the following conditions: bacterial infection; allergy; heart disease; AIDS; Human T-lymphotropic virus 1 infection; Human herpesvirus 3; Human herpesvirus 4; Human papillomavirus; diabetes mellitus; rheumatoid arthritis; Alzheimer's Disease; inflammation; arthritis; asthma; malaria; autoimmune disease; eczema; Lupus erythematosus; psoriasis; rheumatic diseases; Sjogren's syndrome; and viral infection.

The vinca derivatives of the present invention can be administered alone as indicated above, or utilized as biologically active components in pharmaceutical compositions with suitable pharmaceutically acceptable carriers, adjuvants and/or excipients.

In accordance with the present invention, the compounds and/or corresponding compositions can be introduced via different administration routes, which include orally, parenterally, intravenously, intraperitoneally, by intranasal instillation, or by application to mucous membranes, such as, that of the nose, throat, and bronchial tubes.

The active compounds of the present invention may be orally administered, for example, with an inert diluent, or with an assimilable edible carrier, or they may be enclosed in hard or soft shell capsules, or they may be compressed into tablets.

The quantity of the compound administered will vary depending on the patient and the mode of administration and can be any effective amount. The quantity of the compound administered may vary over a wide range to provide in a unit dosage an effective amount of from about 0.01 to 20 mg/kg of body weight of the patient per day to achieve the desired effect. The amount of active compound in such therapeutically useful compositions is such that a suitable dosage will be obtained. Preferred compositions according to the present invention are prepared so that an oral dosage unit contains between about 1 and 250 mg of active compound.

For example, with oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both.

These active compounds and/or pharmaceutical compositions may also be administered parenterally. Solutions of these active compounds and/or compositions can be prepared in water. Dispersions can also be prepared in glycerol, liquid polyethylene glycols, and mixtures thereof in oils.

Illustrative oils are those of animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the pharmaceutical form of the present invention must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds and/or pharmaceutical compositions of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Some of the compounds of the present invention can be in the form of pharmaceutically acceptable acid-addition and/or base salts. All of these forms of salts are within the scope of the present invention.

Pharmaceutically acceptable acid addition salts of the compounds of the present invention include salts derived from nontoxic inorganic acids, such as hydrochloric acid, nitric acid, phosphoric acid, sulfuric acid, hydrobromic acid, hydroiodic acid, hydrofluoric acid, phosphorous acid, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety).

The acid addition salts of said basic compounds are prepared by contacting the free base forms with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediamine, chloroprocaine, choline, diethanolamine, dicyclohexylamine, ethylenedianline, N-methylglucamine, and procaine (see, for example, Berge S. M. et al., "Pharmaceutical Salts," *Journal of Pharmaceutical Science*, 66:1-19 (1997), which is hereby incorporated by reference in its entirety).

The base addition salts of the acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The present invention can be used in conjunction with other known cancer treatments, including other chemotherapeutic agents and radiation.

EXAMPLES

The following examples are provided to illustrate embodiments of the present invention but are no means intended to limit its scope.

Spectroscopic analysis of products described in the experimental procedures below were performed with conventional or standard scientific instrumentation known in the art. Proton NMR spectra were obtained on a Bruker AC 300 spectrometer at 300 MHz or a Bruker 500 MHz spectrometer at 500 MHz and were referenced to tetramethylsilane as an internal standard. Mass spectra were obtained on either a Shimadzu QP-5000 or a PE Sciex API 150 Mass Spectrometer.

Example 1

Preparation of 11'-Bromovinorelbine

A solution of N-iodosuccinimide (288 mg, 1.28 mmol) in trifluoroacetic acid/methylene chloride (1:1, 40 mL) was cooled to approximately 0° C. in an ice water jacketed addition funnel then added dropwise to vinorelbine tartrate (1.35 g, 1.28 mmol) in trifluoroacetic acid/methylene chloride (1:1, 60 mL) at −15° C. The temperature was monitored by an internal thermometer and maintained at −15±3° C. during the course of the addition (45 min). After stirring for 0.5 h, additional N-iodosuccinamide (15 mg, 0.067 mmol) in trifluoroacetic acid/methylene chloride (1:1, 5 mL at 0° C. was added dropwise to drive the reaction to completion. The reaction mixture was then poured carefully into a rapidly stirring mixture of 10% sodium sulfite/chloroform/saturated sodium hydrogencarbonate (1:1:2, 400 mL). Solid sodium hydrogencarbonate was then added in small portions until gas evolution stopped. The solution was then extracted with chloroform (3×100 mL) and the combined extracts were washed with 10% sodium sulfite (50 mL) and brine (50 mL) then dried over magnesium sulfate. The solvent was remove in vacuo to provide 11'-iodovinorelbine (1.21 g, quantitative) as a tan foam which was carried forward without further purification: $^1$H NMR (500 MHz, CD$_3$OD) δ 8.14 (d, J=1.3 Hz, 1H), 7.45 (dd, J=8.6, 1.5 Hz, 1H), 7.21 (d, J=8.6 Hz, 1H), 6.34 (s, 1H), 6.20 (bs, 1H), 5.79-5.87 (m, 2H), 5.28 (d, J=10.4 Hz, 1H), 4.68 (d, J=14.3 Hz, 1H), 4.56 (d, J=14.2 Hz, 1H), 3.94 (d, J=17.0 Hz, 1H), 3.86 (s, 3H), 3.76 (s, 3H), 3.74 (s, 3H), 3.51-3.64 (m, 3H) 3.33 (m, 1H), 3.22 (m, 1H), 3.11 (m, 1H), 2.72 (s, 3H), 2.54-2.72 (m, 5H), 2.31 (m, 1H), 2.04-2.16 (m, 3H), 2.02 (s, 3H), 1.73-1.88 (m, 2H), 1.66 (m, 1H), 1.34 (m, 1H), 1.12 (t, J=7.5 Hz, 3H), 0.67 (t, J=7.3 Hz, 3H); ESI MS m/z 905 [M+H]$^+$.

Example 2

Preparation of 11'-Iodovinorelbine

To an ice cold solution of vinorelbine ditartrate (0.084 g, 0.286 mmol) in trifluoroacetic acid (6 mL) under nitrogen was added a solution of N-iodosuccinimide (0.084 g, 0.365 mmol) in trifluoroacetic acid (3 mL) dropwise and the mixture was stirred at 0° C. for 1.25 hours. The reaction was quenched by the dropwise addition of saturated NaHCO$_3$ and the mixture extracted with dichloromethane. The organic layer was washed with saturated NaHCO$_3$, dried with Na$_2$SO$_4$, filtered and concentrated under reduced pressure. Purification by flash chromatography (silica gel, chloroform to 25% methanol in acetone) gave 11'-iodovinorelbine (220 mg, 85%). $^1$H NMR (500 MHz, CD$_3$OD) δ 8.06 (d, J=1 Hz, 1H), 7.40 (dd, J=9, 1 Hz, 1H), 7.16 (dd, J=9 Hz, 1H), 6.31 (s, 1H), 6.25 (s, 1H), 5.84 (dd, J=10, 4 Hz, 1H), 5.74 (br, 1H), 5.45 (s, 1H), 5.30 (s, 1H), 5.26 (d, J=10 Hz, 1H), 4.31 (d, J=13 Hz, 1H), 4.23 (d, J=13 Hz, 1H), 3.85 (s, 3H), 3.76 (s, 3H), 3.73 (s, 3H), 3.65 (d, J=16 Hz, 1H), 3.58 (s, 1H), 3.35 (s, 1H), 3.37-3.15 (m), 3.00 (q, J=7 Hz, 1H), 2.72 (s, 3H), 2.75-2.50 (m, 3H), 2.58 (s, 1H), 2.31 (m, 2H), 2.15-1.98 (m, 3H), 2.02 (s, 3H), 1.78 (m, 1H), 1.70-1.45 (m, 2H), 1.40-1.20 (m, 1H), 1.09 (t, J=7 Hz, 3H), 0.68 (t, J=7 Hz, 3H); ESI MS m/z 905 [M+H]$^+$.

Example 3

Preparation of 11'-Vinylvinorelbine

A solution of 11'-iodovinorelbine (45 mg, 0.050 mmol) in DME (0.5 mL) and water (0.2 mL) was deoxygenated with argon for 3 minutes. The reaction vessel was charged with 2,4,6-trivinylcyclotriboroxane pyridine complex (13 mg, 0.055 mmol), Pd(PPh$_3$)$_4$ (7.5 mg, 0.070 mmol), and K$_2$CO$_3$ (7.6 mg, 0.055 mmol) and the mixture was heated to 80-90° C. After 2 h, the reaction appeared complete by ESI mass spectral analysis. The reaction mixture was diluted with saturated NaHCO$_3$ (8 mL) and extracted with EtOAc (2×2 mL). The combined extracts were dried (Na$_2$SO$_4$) and concentrated to a brown solid which was purified by flash chromatography (silica gel, [CHCl$_3$/MeOH/NH$_4$OH (40:18:2)]/CH$_2$Cl$_2$, 1:99 to 10:90) to yield 11'-vinylvinorelbine (15 mg, 31%) as a white solid: $^1$H NMR (500 MHz, CD$_3$OD) δ 10.23 (br s, 1H), 7.73 (s, 1H), 7.34 (s, 1H), 6.82 (dd, J=17.5, 11 Hz, 1H), 6.61 (s, 1H), 6.41 (s, 1H), 5.94-5.91 (m, 1H), 5.87-5.86 (m, 1H), 5.74-5.70 (m, 1H), 5.63 (d, J=10.5 Hz, 1H), 5.31 (s, 1H), 5.13-5.11 (m, 1H), 4.93-4.90 (m, 1H), 4.70-4.67 (m, 1H), 4.07 (d, J=17.0 Hz, 1H), 3.94-3.87 (m, 5H), 3.81-3.71 (m, 8H), 3.41 (d, J=16.0 Hz, 1H), 3.19-3.09 (m, 2H), 3.43-3.40 (m, 1H), 3.19-3.09 (m, 2H), 2.85-2.78 (m, 4H), 2.64-2.59 (m, 1H), 2.35-2.29 (m, 1H), 2.18-2.06 (m, 6H), 1.96-1.92 (m, 1H), 1.73-1.69 (m, 1H), 1.49-1.43 (m, 1H), 1.14 (t, J=7.5 Hz, 3H), 0.72 (t, J=7.5 Hz, 3H); ESI MS m/z 805 [M+H]$^+$.

Example 4

Preparation of 11'-(3-Oxohex-1-enyl)vinorelbine

A solution of 11'-iodovinorelbine (0.61 g, 0.674 mmol) in toluene (6 mL) was deoxygenated with argon, Pd(OAc)$_2$ (0.01 g, 0.045 mmol), PPh$_3$ (0.02 g, 0.76 mmol) and triethylamine (0.15 mL, 1.08 mmol) were added and the mixture purged with argon again. The mixture was heated to 70° C., 1-hexen-3-one (0.2 mL, 1.7 mmol) was added and the heating continued for 5 h. The mixture was cooled, deoxygenated again, Pd(OAc)$_2$ (0.01 mg, 0.045 mmol) and 1-hexen-3-one (0.78 mL, 0.67 mmol) were added and the mixture was heated at 75° C. overnight. After cooling to room temperature, the mixture was diluted with EtOAc, filtered, and concentrated under reduced pressure. Purification by reverse phase chromatography (C18; MeCN/water containing 0.05% of NH$_4$OH) gave 11'-(3-oxohex-1-enyl)vinorelbine (18 mg, 31%). $^1$H NMR (300 MHz, CD$_3$OD) δ 8.00 (s, 1H), 7.82 (d, J=16 Hz, 1H), 7.48 (d, J=14 Hz, 1H), 7.35 (d, J=15 Hz, 1H), 7.84 (d, J=16 Hz, 1H), 6.32 (s, 1H), 6.30 (s, 1H), 5.82 (dd, J=10, 4 Hz, 1H), 5.75 (d, J=4 Hz, 1H), 5.30 (s, 1H), 5.27 (d, J=10 Hz, 1H), 4.34 (s, 1H), 3.85 (s, 3H), 3.75 (s, 3H), 3.76-3.70 (m, 1H), 3.73 (s, 3H), 3.64 (m, 1H), 3.57 (s, 1H), 3.45-3.15 (m), 3.00 (m, 2H), 2.72 (s, 3H), 2.75-50 (m, 3H), 2.30 (m, 2H), 2.12-2.02 (m, 3H), 2.02 (s, 3H), 1.93 (s, 1H), 1.80-1.40 (m, 5H), 1.27 (m), 1.10 (t, J=7 Hz, 3H), 1.02 (t, J=7 Hz, 3H), 0.90 (m, 4H), 0.67 (t, J=7 Hz, 3H); ESI MS m/z 875 [M+H]$^+$.

Example 5

Preparation of 11'-(2-tert-Butoxycarbonylvinyl)vinorelbine

Palladium(II) acetate (3.0 mg, 0.012 mmol), triphenylphosphine (6.0 mg, 0.024 mmol), and triethylamine (35 μL, 0.24 mmol) were added to a solution of 11'-iodovinorelbine (107 mg, 0.118 mmol) in toluene (2 mL). The reaction mixture was deoxygenated with an argon purge and tert-butyl acrylate (35 μL, 0.236 mmol) was then added. The reaction mixture was heated to 70° C. overnight. After cooling to room temperature, the reaction mixture was diluted with CH$_2$Cl$_2$ (20 mL), filtered through Celite, and concentrated to dryness. Purification by column chromatography (silica gel, CH$_3$OH/CH$_2$Cl$_2$, 7:93) gave a brown solid (48 mg, 45%) which was further purified by reverse phase chromatography (C18, Waters Symmetry; isocratic 80% acetonitrile/water, 0.05% NH$_4$OH) to give 11'-(2-tert-butoxycarbonylvinyl)vinorelbine as a yellow solid (25 mg, 23%): $^1$H NMR (300 MHz, CD$_3$OD) δ 7.85 (s, 1H), 7.68 (d, J=15.9 Hz, 1H), 7.35 (dd, J=10.5, 1.2 Hz, 1H), 7.26 (d, J=8.5, Hz, 1H), 6.33 (d, J=16.9 Hz, 1H), 6.23 (d, J=6.5 Hz, 2H), 5.75 (dd, J=10.1, 3.6 Hz, 1H), 5.66 (d, J=4.9 Hz, 1H), 5.23 (s, 1H), 5.19 (d, J=10.1 Hz, 1H), 4.26-4.17 (m, 2H), 3.77 (s, 3H), 3.68 (s, 3H), 3.65 (s, 3H), 3.58-3.50 (m, 3H), 3.30-3.08 (m, 3H), 2.93 (dd, J=15.4, 7.5 Hz, 1H), 2.64 (s, 3H), 2.64-2.41 (m, 3H), 2.24-2.14 (m, 2H), 2.09-1.86 (m, 3H), 1.94 (s, 3H), 1.76-1.68 (m, 1H), 1.62-1.37 (m, 2H), 1.47 (s, 9H), 1.32-1.21 (m, 1H), 1.02 (t, J=7.4 Hz, 3H), 0.62 (t, J=7.3 Hz, 3H); ESI MS m/z 905 [M+H]$^+$.

Example 6

Preparation of 11'-(Carboxyvinyl)vinorelbine Trifluoroacetate

A solution of 11'-(2-tert-butoxycarbonyl-vinyl)vinorelbine (25 mg, 0.03 mmol) in CH$_2$Cl$_2$ (1.0 mL) was treated with TFA (0.3 mL) at 0° C. and then stirred at room temperature for 1 h. The reaction mixture was poured slowly into saturated NaHCO$_3$ (30 mL) and the mixture was extracted with CH$_2$Cl$_2$ (60 mL). The organic layer was washed with brine, dried over Na$_2$SO$_4$, and concentrated to give a yellow solid (19 mg, 83%). The solid was treated with CH$_2$Cl$_2$ (1 mL) and a drop of trifluoroacetic acid. The solution was evaporated to give 11'-(carboxyvinyl)vinorelbine trifluoroacetate as a yellow solid (23.6 mg, 98%): $^1$H NMR (300 MHz, CD$_3$OD) δ 10.38 (s, 1H), 7.86 (s, 1H), 7.72 (d, J=15.9 Hz, 1H), 7.38-7.29 (m, 2H), 6.57 (s, 1H), 6.35 (d, J=15.9 Hz, 1H), 6.31 (s, 1H), 5.82 (dd, J=9.9, 4.3 Hz, 1H), 5.81-5.77 (m, 1H), 5.54 (d, J=9.8 Hz, 1H), 5.20 (s, 1H), 4.84 (d, J=14.5 Hz, 1H), 4.58 (d, J=14.5 Hz, 1H), 4.02-3.83 (m, 3H), 3.79 (s, 3H), 3.71 (s, 3H), 3.66 (s, 3H), 3.71-3.62 (m, 4H), 3.32 (d, J=12.5 Hz, 1H), 3.14-2.97 (m, 2H), 2.76-2.69 (m, 1H), 2.69 (s, 3H), 2.57-2.48 (m, 1H), 2.25-2.16 (m, 1H), 2.10-2.02 (m, 4H), 1.96 (s, 3H), 1.63-1.54 (m, 1H), 1.41-1.34 (m, 1H), 1.04 (t, J=7.4 Hz, 3H), 0.61 (t, J=7.2 Hz, 3H); ESI MS m/z 849 [M+H]$^+$.

Example 7

Preparation of 11'-(Methoxycarbonylethylsulfanyl) vinorelbine vinorelbine Tartrate Step 1: A flask containing 11'-iodovinorelbine (113 mg, 0.13 mmol), 1,1'-bis(diphenylphosphino)ferrocene (28 mg, 0.05 mmol), and tris(dibenzylideneacetone)dipalladium(0) (11.4 mg, 0.012 mmol) was deoxygenated with nitrogen then triethylamine (35 μL, 0.25 mmol) and NMP (1.1 mL) were added via syringe. The resulting solution was purged again with nitrogen before the addition of methyl 3-mercaptopropionate (28 μL, 0.25 mmol). The mixture was heated at 60° C. for 4 h. After cooling, the reaction mixture was diluted with ethyl acetate, washed with water and brine, dried over Na$_2$SO$_4$, and concentrated under vacuum. Purification by flash chromatography (silica gel, CHCl$_3$/MeOH/Et$_3$N=99:1: 0.5), followed by reverse phase chromatography (C18; MeCN/water with 0.1% of TFA) gave 11'-(methoxycarbonylethylsulfanyl)vinorelbine trifluoroacetate (22 mg, 21%). $^1$H NMR (500 MHz, MeOD) δ 7.85 (d, J=1 Hz, 1H), 7.31 (d, J=8 Hz, 1H), 7.25 (dd, J=8, 2 Hz, 1H), 6.32 (s, 1H), 6.28 (s, 1H), 5.83 (dd, J=10, 4 Hz, 1H), 5.76 (d, J=4 Hz, 1H), 5.31 (s, 1H), 5.27 (d, J=10 Hz, 1H), 4.38 (s, 2H), 3.85 (s, 3H), 3.76 (s, 3H), 3.76-3.70 (m, 1H), 3.73 (s, 3H), 3.64 (s, 3H), 3.58 (s, 1H), 3.41 (d, J=14 Hz, 1H), 3.37-3.32 (m), 3.21 (td, J=9, 5 Hz, 1H), 3.11 (t, J=7 Hz, 2H), 3.03 (dd, J=16, 8 Hz, 1H), 2.72 (s, 3H), 2.65 (br d, J=16 Hz, 1H), 2.62-2.55 (m, 4H), 2.40 (br dd, J=13, 5 Hz, 1H), 2.27 (td, J=10, 6 Hz, 1H), 2.12-2.02 (m, 3H), 2.02 (s, 3H), 1.79 (ddd, J=13, 11, 5 Hz, 1H), 1.63 (dd, J=14, 7 Hz, 1H), 1.62-1.58 (m, 1H), 1.32 (dd, J=14, 7 Hz, 1H), 1.10 (t, J=7 Hz, 3H), 0.69 (t, J=7 Hz, 3H); ESI MS m/z 898 [M+H]$^+$.

Step 2: To a stirred solution of 11'-[3-(methyl 3-mercaptopropionoate)]vinorelbine (16 mg, 0.018 mmol) in ether/MeOH (2.0 mL/0.2 mL) at room temperature was added a solution of L-tartaric acid (5.9 mg, 0.039 mmol) ether/MeOH (2.0 mL/0.2 mL) and the resulting slurry was stirred at room temperature for 10 min, and refluxed for 12 min. Another 2 mL of ether was added and the mixture cooled to 0° C. The solid was collected by filtration, washed with ether, and dried under vacuum to give the tartrate salt (9.2 mg, 43%); mp: 140-170° C. (dec.); $^1$H NMR (500 MHz, MeOD) δ 7.92 (s, 1H), 7.39 (d, J=8 Hz, 1H), 7.31 (dd, J=8, 1 Hz, 1H), 6.36 (s, 1H), 6.30 (s, 1H), 5.90-5.84 (m, 2H), 5.33 (d, J=10 Hz, 1H), 5.29 (s, 1H), 4.93 (d, J=15 Hz, 1H), 4.68 (d, J=15 Hz, 1H), 4.43 (s, 3.4H), 4.12 (d, J=17 Hz, 1H), 3.87 (s, 3H), 3.77 (s, 3H), 3.75 (s, 3H), 3.78-3.74 (m, 1H), 3.68 (br d, J=14 Hz, 1H), 3.64 (s, 3H), 3.61 (s, 1H), 3.40 (dd, J=16, 5 Hz, 1H), 3.15 (t, J=7 Hz, 2H), 3.13 (m, 1H), 2.88 (dd, J=13, 4 Hz, 1H), 2.80-2.73 (m, 2H), 2.74 (s, 3H), 2.65-2.54 (m, 1H), 2.61 (t, J=7 Hz, 2H), 2.48-2.40 (m, 1H), 2.19-2.09 (m, 3H), 2.03 (s, 3H), 1.99-1.91 (m, 1H), 1.86-1.78 (m, 1H), 1.64 (m, 1H), 1.36 (m, 1H), 1.14 (t, J=7 Hz, 3H), and 0.69 (t, J=7 Hz, 3H); ESI MS m/z 898 [M+H]$^+$.

Example 8

Preparation of 11'-Thiovinorelbine Trifluoroacetate

11'-Iodovinorelbine (44 mg, 0.049 mmol), thiotriisopropylsilyl potassium salt (33 mg, 0.156 mmol), and tetrakis(triphenylphosphine) palladium(0) (11 mg, 0.010 mmol) were combined in benzene/tetrahydrofuran (2.5 mL, 4:1) and the reaction was deoxygenated by bubbling argon through the solution for 30 min. The mixture was heated to 65° C. for 1 h then diluted with ethyl acetate (15 mL). The organic solution was washed with saturated NaHCO$_3$ (2×5 mL) and brine (5 mL), dried over MgSO$_4$, and evaporated to dryness in vacuo. The residue was purified by reverse phase chromatography (C18, acetonitrile/water, 0.05% TFA) to provide 11'-thiovinorelbine trifluoroacetate (22.7 mg, 45% yield) as a white powder after lyophilization: $^1$H NMR (500 MHz, CD$_3$OD) δ 10.24 (bs, 1H), 7.70 (s, 1H), 7.28 (d, J=8.4 Hz, 1H), 7.13 (dd, J=8.5, 1.7 Hz, 1H), 6.61 (s, 1H), 6.41 (s, 1H), 5.92 (m, 1H), 5.86 (m, 1H), 5.62 (d, J=10.5 Hz, 1H), 5.30 (s, 1H), 4.84 (m, 1H), 4.64 (d, J=14.5, 1H), 4.06 (d, J=16.9 Hz, 1H), 3.94-3.68 (m, 6H), 3.88 (s, 3H), 3.81 (s, 3H), 3.75 (s, 3H), 3.40 (d, J=15.4 Hz, 1H), 3.14 (m, 3H), 2.81 (m, 1H), 2.78 (s, 3H), 2.59 (m, 1H), 2.30 (m, 1H), 2.15 (q, J=7.4 Hz, 2H), 2.06 (s, 3H), 1.93 (m, 1H), 1.68 (m, 1H), 1.46 (m, 1H), 1.13 (t, J=7.5 Hz, 3H), 0.70 (t, J=7.3 Hz, 3H); ESI MS m/z 811 [M+H]$^+$.

Example 9

Preparation of 11'-(Methoxycarbonylmethylsulfanyl) vinorelbine Trifluoroacetate Methyl thioglycolate (63 mg, 0.596 mmol), 11'-iodovinorelbine (54 mg, 0.060 mmol), triethylamine (145 mg, 1.43 mmol) and tris(dibenzylideneacetone)dipalladium(0) (5.4 mg, 0.006 mmol) were combined in N-methyl-2-pyrrolidinone (1.5 mL) and the reaction mixture was deoxygenated by bubbling argon through the solution for 30 min. The mixture was heated at 60° C. for 8 h then diluted with ethyl acetate (20 mL). The organic solution was washed with saturated NaHCO$_3$ (2×5 mL) and brine (5 mL), dried over MgSO$_4$, and evaporated to dryness in vacuo. The residue was purified by reverse phase chromatography (C18, acetonitrile/water, 0.05% TFA) to provide 11'-(methoxycarbonylmethylsulfanyl)vinorelbine trifluoroacetate (5.8 mg, 9% yield) as a white powder after lyophilization: $^1$H NMR (500 MHz, CD$_3$OD) δ 10.38 (bs, 1H), 7.90 (s, 1H), 7.36 (d, J=8.5 Hz, 1H), 7.30 (dd, J=8.5, 1.6 Hz, 1H), 6.63 (s, 1H), 6.41 (s, 1H), 5.93 (dd, J=10.4, 5.4 Hz, 1H), 5.87 (d, J=4.1 Hz, 1H), 5.62 (d, J=10.4 Hz, 1H), 5.31 (s, 1H), 4.88 (d, J=14.7 Hz, 1H), 4.67 (d, J=14.5, 1H), 4.08 (d, J=16.8 Hz, 1H), 3.95-3.55 (m, 8H), 3.88 (s, 3H), 3.81 (s, 3H), 3.75 (s, 3H), 3.65 (s, 3H), 3.39 (m, 1H), 3.14 (m, 2H), 2.83 (dd, J=13.7, 4.5 Hz, 1H), 2.78 (s, 3H), 2.63 (m, 1H), 2.31 (m, 1H), 2.16 (q, J=7.5 Hz, 2H), 2.08 (m, 1H), 2.06 (s, 3H), 1.94 (m, 1H), 1.70 (m, 1H), 1.47 (m, 1H), 1.14 (t, J=7.5 Hz, 3H), 0.70 (t, J=7.3 Hz, 3H); ESI MS m/z 883 [M+H]$^+$.

Example 10

Preparation of 11'-(Methylsulfanyl)vinorelbine Trifluoroacetate

11'-Iodovinorelbine (70 mg, 0.077 mmol), tris(dibenzylideneacetone)dipalladium(0) (11 mg, 0.011 mmol), 1,1'-bis(diphenylphosphino)ferrocene (26 mg, 0.046 mmol), 1-methyl-2-pyrrolidinone (0.5 mL), and triethylamine (22 μL) were combined in a resealable glass test tube. Argon was bubbled through the solution for 10 min. Methanethiol (0.29 mL of a 4 N solution in NMP, 1.2 mmol) was added, the test tube sealed, and the mixture was heated to 65° C. After 5 h, additional methanethiol (0.39 mL of a 4 N solution in NMP, 1.5 mmol) was added, and the mixture was heated to 65° C. overnight. After cooling, the mixture was diluted with ethyl acetate (75 mL), washed with saturated NH$_4$Cl (3×15 mL), water and brine, then dried (Na$_2$SO$_4$) and evaporated to dryness under vacuum. The residue was purified by reverse phase chromatography (C18, acetonitrile/water, 0.05% TFA) to provide 11'-(methylsulfanyl)vinorelbine trifluoroacetate (10 mg, 12% yield) as a white powder after lyophilization: $^1$H NMR (500 MHz, CD$_3$OD) δ 10.25 (br s, 1H), 7.71 (d, J=1.0 Hz, 1H), 7.33 (d, J=8.5 Hz, 1H), 7.18 (dd, J=8.5, 1.5 Hz, 1H), 6.63 (s, 1H), 6.41 (s, 1H), 5.93 (dd, J=10.5, 4.5 Hz, 1H), 5.87 (d, J=4.5 Hz, 1H), 5.63 (d, J=10.5 Hz, 1H), 5.31 (s, 1H), 4.90 (d, J=14.5 Hz, 1H), 4.67 (d, J=14.5 Hz, 1H), 4.07 (d, J=16.5 Hz, 1H), 3.95-3.88 (m, 4H), 3.83 (s, 3H), 3.81-3.71 (m, 7H), 3.44-3.40 (m, 1H), 3.19-3.08 (m, 2H), 2.83 (dd, J=13.5, 4.5 Hz, 1H), 2.74 (s, 3H), 2.64-2.58 (m, 1H), 2.49 (s, 3H), 2.35-2.29 (m, 1H), 2.18-2.06 (m, 6H), 1.98-1.91 (m, 1H), 1.73-1.68 (m, 1H), 1.48-1.43 (m, 1H), 1.14 (t, J=7.5 Hz, 3H), 0.71 (t, J=7.3 Hz, 3H); ESI MS m/z 825 [M+H]$^+$.

Example 11

Preparation of 11'-(Ethylsulfanyl)vinorelbine Trifluoroacetate

A solution of 11'-iodovinorelbine (70 mg, 0.07 mmol) in NMP (1.5 mL) was deoxygenated with argon for 10 minutes. The reaction vessel was charged with 1,1'-bis(diphenylphosphino)ferrocene (20 mg, 0.035 mmol), tris(dibenzylideneacetone)dipalladium(0) (10 mg, 0.011 mmol) and Et$_3$N (0.10 mL, 0.72 mmol). The mixture was stirred for 20 min at room temperature, and then ethanethiol (0.10 mL, 1.3 mmol) was added and then stirred at 60° C. overnight. The mixture was cooled to room temperature, diluted with EtOAc (100 ml) and washed with saturated NH$_4$Cl (3×10 mL) and brine (3×10 mL), dried (Na$_2$SO$_4$) and concentrated. The residue was filtered through a pad of silica gel, eluted with CH$_2$Cl$_2$/MeOH (4:1, 2×100 mL). The filtration was concentrated, purified by reverse phase chromatography (C-18, acetonitrile/water, 0.05% TFA) to give 11'-(ethylsulfanyl)vinorelbine trifluoroacetate (10 mg, 15%) as a light yellow solid: $^1$H NMR (500 MHz, CD$_3$OD) δ 10.29 (s, 1H), 7.81 (s, 1H), 7.34 (d, J=8.5 Hz, 1H), 7.23 (dd, J=8.5, 1.5 Hz, 1H), 6.67 (s, 1H), 6.41 (s, 1H), 5.93 (dd, J=10.5, 5.0 Hz, 1H), 5.86 (d, J=4.5 Hz, 1H), 5.63 (d, J=10.5 Hz, 1H), 5.31 (s, 1H), 4.90 (d, J=14.5 Hz, 1H), 4.65 (d, J=14.5 Hz, 1H), 4.06 (d, J=17 Hz, 1H), 3.93 (dd, J=15.0, 4.5 Hz, 2H), 3.89 (s, 3H), 3.81 (s, 3H), 3.78 (s, 2H), 3.75 (s, 3H), 3.72 (s, 1H), 3.43 (d, J=15.5 Hz, 1H), 3.24-3.16 (m, 1H), 3.10 (dd, J=15.5, 7.5 Hz, 1H), 2.90 (q, J=7.0 Hz, 2H), 2.82 (dd, J=13.5, 4.5 Hz, 1H), 2.79 (s, 3H), 2.61 (dd, J=15.5, 12.5 Hz, 1H), 2.36-2.28 (m, 1H), 2.16 (q, J=7.5 Hz, 2H), 2.07 (s, 3H), 1.97-1.89 (m, 1H), 1.70 (dd, J=14.5, 7.5 Hz, 1H), 1.47 (dd, J=14.5, 7.5 Hz, 1H), 1.90-1.85 (m, 1H), 1.70 (dd, J=14.5, 7.5 Hz, 1H), 1.47 (dd, J=14.5, 7.5 Hz, 1H), 1.24 (t, J=7.0 Hz, 3H), 1.13 (t, J=7.5 Hz, 3H), 0.71 (t, J=7.0 Hz, 3H); ESI MS m/z 839 [M+H]$^+$.

Example 12

Preparation of 11'-(4-Hydroxybutylsulfanyl)vinorelbine 1,1'-Bis(diphenylphosphino)ferrocene (8 mg, 0.014 mmol), tris(dibenzylideneacetone)dipalladium(0) (3.0 mg, 0.004 mmol), and triethylamine (10 μL, 0.07 mmol) were added to a solution of 11'-iodovinorelbine (31.6 mg, 0.035 mmol) in NMP (1 mL). The reaction mixture was deoxygenated with an argon purge and 4-mercapto-1-butanol (8 μL, 0.07 mmol) was then added. The reaction mixture was heated to 60° C. overnight. After cooling to room temperature, the reaction mixture was diluted with CH$_2$Cl$_2$ (20 mL), washed with water and brine, then dried over Na$_2$SO$_4$ and concentrated to an oily residue. Purification by column chromatography (silica gel, CH$_3$OH/CH$_2$Cl$_2$, 5:95) gave a brown solid (13 mg, 42%) which was further purified by reverse phase chromatography (C18, Waters Symmetry; isocratic 70% acetonitrile/water, 0.05% NH$_4$OH) to give 11'-(4-hydroxybutylsulfanyl)vinorelbine as a brown solid (9 mg, 30%): $^1$H NMR (300 MHz, CD$_3$OD) δ 7.70 (s, 1H), 7.18-7.10 (m, 2H), 6.21 (d, J=5.2 Hz, 2H), 5.73 (dd, J=10.1, 3.7 Hz, 1H), 5.64 (d, J=4.4 Hz, 1H), 5.21 (s, 1H), 5.16 (d, J=10.1 Hz, 1H). 4.21-4.15 (m, 2H), 3.75 (s, 3H), 3.65 (s, 3H), 3.62 (s, 3H), 3.58-3.41 (m, 4H), 3.30-3.08 (m, 2H), 2.90 (dd, J=15.6, 6.6 Hz, 1H), 2.84-2.80 (m, 2H), 2.61 (s, 3H), 2.57-2.43 (m, 3H), 2.23-2.11 (m, 2H), 2.02-1.91 (m, 3H), 1.91 (s, 3H), 1.75-1.50 (m, 6H), 1.41-1.18 (m, 5H), 0.99 (t, J=7.4 Hz, 3H), 0.59 (t, J=7.2 Hz, 3H); ESI MS m/z 883 [M+H]$^+$.

Example 13

Preparation of 11'-(3-Hydroxypropylsulfanyl)vinorelbine 1,1'-Bis(diphenylphosphino)ferrocene (12 mg, 0.022 mmol), tris(dibenzylideneacetone)dipalladium(0) (5.0 mg, 0.006 mmol), and triethylamine (15 μL, 0.11 mmol) were added to a solution of 11'-iodovinorelbine (50 mg, 0.055 mmol) in NMP (1 mL). The reaction mixture was deoxygenated with an argon purge and 3-mercapto-1-propanol (10 μL, 0.11 mmol) was then added. The reaction mixture was heated to 60° C. overnight. After cooling to room temperature, the reaction mixture was diluted with CH$_2$Cl$_2$ (20 mL), washed with water and brine, then dried over Na$_2$SO$_4$ and concentrated to an oily residue. Purification by column chromatography (silica gel, CH$_3$OH/CH$_2$Cl$_2$, 7:93) gave a brown solid (20 mg, 42%) which was further purified by reverse phase chromatography (C18, Waters Symmetry; isocratic 70% acetonitrile/water, 0.05% NH$_4$OH) to give 11'-(3-hydroxypropylsulfanyl)vinorelbine as a brown solid (10 mg, 19%): $^1$H NMR (300 MHz, CD$_3$OD) δ 7.81 (s, 1H), 7.29-7.21 (m, 2H), 6.33 (s, 2H), 5.84 (dd, J=10.4, 4.0 Hz, 1H), 5.75 (d, J=4.0 Hz, 1H), 5.32 (s, 1H), 5.28 (d, J=10.1 Hz, 1H). 4.32-4.21 (m, 2H), 3.86 (s, 3H), 3.77 (s, 3H), 3.73 (s, 3H), 3.69-3.58 (m, 3H), 3.39-3.19 (m, 2H), 2.98 (dd, J=7.1, 7.3 Hz, 3H), 2.72 (s, 3H), 2.69-2.54 (m, 3H), 2.33-2.23 (m, 2H), 2.11-2.03 (m, 3H), 2.03 (s, 3H), 1.81 (dd, J=7.3, 6.8 Hz, 2H), 1.86-1.76 (m, 1H), 1.71 (dd, J=7.9, 7.1 Hz, 1H), 1.63 (dd, J=6.9, 7.4 Hz, 1H), 1.53-1.43 (m, 1H), 1.36-1.30 (m, 3H), 1.10 (t, J=7.5 Hz, 3H), 0.71 (t, J=7.2 Hz, 3H); ESI MS m/z 869 [M+H]$^+$.

Example 14

Preparation of 11'-(2-Hydroxyethylsulfanyl)vinorelbine 1,1'-Bis(diphenylphosphino)ferrocene (12 mg, 0.022 mmol), tris(dibenzylideneacetone)dipalladium(0) (5.0 mg, 0.006 mmol), and triethylamine (15 μL, 0.11 mmol) were added to a solution of 11'-iodovinorelbine (50.5 mg, 0.056 mmol) in NMP (1 mL). The reaction mixture was deoxygenated with an argon purge and 2-mercaptoethanol (8 μL, 0.11 mmol) was then added. The reaction mixture was heated to 60° C. for 4 h. After cooling to room temperature, the reaction mixture was diluted with CH$_2$Cl$_2$ (20 mL), washed with water and brine, then dried over Na$_2$SO$_4$ and concentrated to an oily residue. Purification by column chromatography (silica gel, CH$_3$OH/CH$_2$Cl$_2$, 5:95) gave a brown solid (20 mg, 42%) which was further purified by reverse phase chromatography (C18, isocratic 70% acetonitrile/water, 0.05% NH$_4$OH) to give 11'-(2-hydroxyethylsulfanyl)vinorelbine as a brown solid (7 mg, 15%): $^1$H NMR (300 MHz, CD$_3$OD) δ 7.76 (s, 1H), 7.23-7.15 (m, 2H), 6.23 (d, J=2.1 Hz, 2H), 5.76 (dd, J=10.1, 3.5 Hz, 1H), 5.66 (d, J=4.4 Hz, 1H), 5.23 (s, 1H), 5.19 (d, J=10.2 Hz, 1H). 4.25-4.14 (m, 2H), 3.77 (s, 3H), 3.68 (s, 3H), 3.64 (s, 3H), 3.61-3.50 (m, 4H), 3.30-3.09 (m, 2H), 2.93 (dd, J=7.0, 6.8 Hz, 3H), 2.64 (s, 3H), 2.67-2.46 (m, 3H), 2.24-2.14 (m, 2H), 2.09-1.94 (m, 3H), 1.94 (s, 3H), 1.54 (dd, J=7.0, 7.5 Hz, 1H), 1.39 (dd, J=7.8, 7.6 Hz, 1H), 1.81-1.21 (m, 5H), 1.01 (t, J=7.4 Hz, 3H), 0.62 (t, J=7.2 Hz, 3H); ESI MS m/z 855 [M+H]$^+$.

Example 15

Preparation of 11'-(2-Fluorophenylmethyl)vinorelbine Trifluoroacetate

A solution of 11'-iodovinorelbine (70 mg, 0.07 mmol) in NMP (1.5 mL) was deoxygenated with argon for 10 minutes. The reaction vessel was charged with 1,1'-bis(diphenylphosphino)ferrocene (20 mg, 0.035 mmol), tris(dibenzylideneacetone)dipalladium(0) (10 mg, 0.011 mmol) and Et$_3$N (0.10 mL, 0.13 mmol). The mixture was stirred for 20 min at room temperature, and then 2-fluorophenylmethane-thiol (20 mg, 0.141 mmol) was added and then stirred at 60° C. overnight. The mixture was cooled to room temperature, diluted with EtOAc (100 ml) and washed with saturated NH$_4$Cl (3×10 mL) and brine (3×10 mL). The organic layer was dried (Na$_2$SO$_4$), filtered, and concentrated. The residue was filtered through a pad of silica gel, eluted with CH$_2$Cl$_2$/MeOH (4:1, 2×100 mL). Purification by reverse phase chromatography (C18, acetonitrile/water, 0.05% TFA) gave 11'-(2-fluorobenzylsulfanyl)vinorelbine trifluoroacetate as an off-white solid (3 mg, 4%): $^1$H NMR (500 MHz, CD$_3$OD) δ 10.38 (s, 1H), 7.82 (s, 1H), 7.38 (dt, J=8.0, 1.5 Hz, 1H), 7.32 (d, J=8.5 Hz, 1H), 7.26-7.03 (m, 4H), 6.16 (s, 1H), 6.41 (s, 1H), 5.94 (dd, J=10.5, 4.0 Hz, 1H), 5.86 (d, J=4.5 Hz, 1H), 5.64 (d, J=11 Hz, 1H), 5.31 (s, 1H), 4.72 (dd, J=8.5, 4.0 Hz, 1H), 4.66 (d, J=14.5 Hz, 1H), 4.15-4.05 (m, 3H), 3.95-3.84 (m, 3H), 3.81 (s, 3H), 3.76 (s, 3H), 3.75-3.72 (m, 3H), 3.46-3.42 (m, 1H), 3.22-3.18 (m, 1H), 3.08 (dd, J=16.8, 8.0 Hz, 1H), 2.84-2.81 (m, 1H), 2.78 (s, 3H), 2.74 (s, 3H), 2.64-2.44 (m, 2H), 2.38-2.31 (m, 2H), 2.21-2.13 (m, 2H), 2.06 (s, 3H), 1.70 (dd, J=14.5, 7.2 Hz, 1H), 1.46 (dd, J=15.0, 7.5 Hz, 1H), 1.13 (t, J=7.5 Hz, 3H), 0.71 (t, J=7.5 Hz, 3H); ESI MS m/z 919 [M+H]$^+$.

Example 16

Preparation of 11'-(2-Chlorophenylmethyl)vinorelbine Trifluoroacetate

A solution of 11'-iodovinorelbine (70 mg, 0.07 mmol) in NMP (1.5 mL) was deoxygenated with argon for 10 minutes. The reaction vessel was charged with 1,1'-bis(diphenylphosphino)ferrocene (20 mg, 0.036 mmol), tris(dibenzylideneacetone)dipalladium(0) (10 mg, 0.01 mmol) and Et$_3$N (0.10 mL, 0.13 mmol). The mixture was stirred for 20 min at room temperature, and then 2-chlorobenzenmethanethiol (0.10 mL, 0.75 mmol) was added and then stirred at 60° C. overnight. The mixture was cooled to room temperature, diluted with methylene chloride (100 mL) and washed with saturated NH$_4$Cl (3×10 mL) and brine (3×10 mL), dried over Na$_2$SO$_4$, and evaporated to dryness in vacuo. The residue was purified by flash chromatography (silica gel, CH$_2$Cl$_2$/MeOH 10:1) and then by reverse phase chromatography (C18, acetonitrile/water, 0.05% TFA) to give 111'-(2-chlorobenzylsulfanyl)vinorelbine trifluoroacetate (9 mg, yield 12%) as a light yellow solid: $^1$H NMR (500 MHz, CD$_3$OD) δ10.35 (s, 1H), 7.80 (s, 1H), 7.36 (dd, J=8.5, 1.0 Hz, 1H), 7.31 (d, J=8.5 Hz, 1H), 7.20-7.17 (m, 2H), 7.12-7.01 (m, 2H), 6.63 (s, 1H), 6.41 (s, 1H), 5.94 (dd, J=10.5, 5.0 Hz, 1H), 5.86 (d, J=4.5 Hz, 1H), 5.64 (d, J=10.5 Hz, 1H), 5.30 (s, 1H), 4.98 (d, J=14.5 Hz, 1H), 4.65 (d, J=14.5 Hz, 1H), 4.22 (d, J=13.0 Hz, 1H), 4.15 (d, J=12.5 Hz, 1H), 4.05 (d, J=16.5 Hz, 1H), 3.93 (dd, J=15.5, 5.5 Hz, 2H), 3.88 (s, 3H), 3.81 (s, 3H), 3.76 (s, 3H), 3.75-3.72 (m, 2H), 3.71 (s, 2H), 3.42 (d, J=16.0 Hz, 1H), 3.20-3.14 (m, 1H), 3.09 (dd, J=16.0, 7.5 Hz, 1H), 2.83-2.79 (m, 1H), 2.78 (s, 3H), 2.64-2.57 (m, 1H), 2.34-2.27 (m, 1H), 2.15 (q, J=7.0 Hz, 2H), 2.06 (s, 3H), 1.98-1.88 (m, 1H), 1.70 (dd, J=14.5, 7.5 Hz, 1H), 1.47 (dd, J=14.5, 7.5 Hz, 1H), 1.29 (s, 1H), 1.13 (t, J=7.5 Hz, 3H), 0.92-0.83 (m, 1H), 0.70 (t, J=7.5 Hz, 3H); ESI MS m/z 935 [M+H]$^+$.

Example 17

Preparation of 11'-(Phenylsulfanyl)vinorelbine Ditartrate

Step 1: To a deoxygenated solution of 11'-iodovinorelbine (105 mg, 0.116 mmol) in NMP (2.5 mL) was added 1,1'-bis(diphenylphosphino)ferrocene (36 mg, 0.065 mmol), tris(dibenzylideneacetone)dipalladium(0) (16 mg, 0.017 mmol) and Et$_3$N (33 μL, 0.24 mmol). The mixture was stirred for 10 min at room temperature, benzenethiol (26 mg, 0.232 mmol) was added and the mixture was stirred at 60° C. overnight (16 h), then cooled to room temperature, diluted with methylene chloride (15 ml) and washed with saturated NH$_4$Cl (5 mL). The organic layer was dried (Na$_2$SO$_4$), filtered, and concentrated. Purification by plug chromatography (silica gel, MeOH/CH$_2$Cl$_2$, 3:97), followed by reverse phase chromatography (C18 column, CH$_3$CN, H$_2$O, 0.05% NH$_4$OH) and then flash chromatography (silica gel, MeOH/CHCl$_3$, 1:99) afforded 11'-(phenylsulfanyl)vinorelbine (23 mg, 22%) as a pale yellow solid: mp 202-206° C.; $^1$H NMR (500 MHz, CD$_3$OD) δ 7.89 (d, J=2 Hz, 1H), 7.35 (d, J=6 Hz, 1H), 7.25 (d, J=6 Hz, 1H), 7.22-7.16 (m, 2H), 7.16-7.07 (m, 3H), 6.32 (s, 1H), 6.31 (s, 1H), 5.84 (dd, J=6, 5 Hz, 1H), 5.73 (s, 1H), 5.32 (s, 1H), 5.27 (d, J=10 Hz, 1H), 4.31 (d, J=13 Hz, 1H), 4.23 (d, J=12 Hz, 1H), 3.85 (s, 3H), 3.76 (s, 3H), 3.74 (s, 3H), 3.61 (br s, 1H), 3.58 (s, 1H), 3.37 (d, J=15 Hz, 1H), 3.25-3.16 (m, 2H), 3.00 (dd, J=15, 7 Hz, 1H), 2.72 (s, 3H), 2.68-2.55 (m, 3H), 2.32-2.33 (m, 2H), 2.12-2.04 (m, 3H), 2.02 (s, 3H), 1.85-1.77 (m, 1H), 1.68-1.59 (m, 1H), 1.53 (br s, 1H), 1.39-1.25 (m, 2H), 1.04-1.10 (m, 3H), 0.70 (t, J=7 Hz, 3H); ESI MS m/z 887 [M+H]$^+$.

Step 2: To a solution of 11'-(phenylsulfanyl)vinorelbine (9.9 mg, 0.0112 mmol) in MeOH (100 μL) and Et$_2$O (2 mL) was added a solution of L-tartaric acid (4.5 mg, 0.030 mmol) in MeOH (120 μL) and Et$_2$O (2 mL). The solid was collected by filtration to yield 11'-(phenysulfanyl)vinorelbine ditartrate (10.5 mg, 79%) as a white solid: mp 239-242° C. (dec); $^1$H NMR (500 MHz, CD$_3$OD) δ 8.04 (br s, 1H), 7.45 (d, J=8 Hz, 1H), 7.32 (d, J=8 Hz, 1H), 7.23 (t, J=7 Hz, 2H), 7.17 (d, J=7 Hz, 2H), 7.14 (t, J=7 Hz, 1H), 6.37 (s, 1H), 6.33 (br s, 1H), 5.88 (s, 2H), 5.34 (d, J=10 Hz, 1H), 5.30 (s, 1H), 4.90 (m), 4.69 (d, J=14 Hz, 1H), 4.44 (s, 4H), 4.08 (d, J=17 Hz, 1H), 3.88 (s, 3H) 3.77 (s, 3H), 3.76 (s, 3H), 3.76-3.70 (m, 2H), 3.62 (s, 1H), 3.44 (d, J=16 Hz, 1H), 3.15 (dd, J=15, 7 Hz, 1H), 2.94-2.76 (m, 3H), 2.74 (s, 3H), 2.62 (t, J=12 Hz, 1H), 2.47 (br m, 1H), 2.19-2.09 (m, 3H), 2.03 (s, 3H), 1.96 (br s, 1H), 1.84 (br s, 1H), 1.69-1.60 (m, 1H), 1.43-1.33 (m, 1H), 1.13 (t, J=7 Hz, 3H), 0.70 (t, J=7 Hz, 3H); ESI MS m/z 887 [M+H]$^+$.

Example 18

Preparation of 11'-(3-Hydroxyphenysulfanyl)vinorelbine Ditartrate

Step 1: To a flask containing 11'-iodovinorelbine (100 mg, 0.111 mmol) was added 1,1'-bis(diphenylphosphino)ferrocene (36 mg, 0.065 mmol), tris(dibenzylideneacetone)dipalladium(0) (15 mg, 0.016 mmol) NMP (2.0 mL) and Et$_3$N (33 μL, 0.24 mmol). The mixture was stirred for 10 min at room temperature. A solution of 3-hydroxythiophenol (28 mg, 0.22 mmol) in NMP (0.5 mL) was added and the mixture was stirred at 60° C. overnight (16 h). The mixture was cooled to room temperature, diluted with methylene chloride (15 ml) and saturated NH$_4$Cl (5 mL) was added. The organic layer was dried (Na$_2$SO$_4$), filtered, and concentrated. Purification by plug chromatography (silica gel, eluent: MeOH/CH$_2$Cl$_2$, 3:97) followed by reverse phase chromatography (C8 column, CH$_3$CN, H$_2$O, 0.05% NH$_4$OH), flash chromatography (silica gel, 0.5% to 4% MeOH/CHCl$_3$), and then reverse phase chromatography (C18, H$_2$O, CH$_3$CN, 0.1% TFA) gave 11'-(3-hydroxyphenysulfanyl)vinorelbine trifluoroacetate (10 mg, 10%) as a white solid: mp 236-242° C. (dec); $^1$H NMR (500 MHz, CD$_3$OD) δ 7.93 (s, 1H), 7.36 (d, J=8 Hz, 1H), 7.27 (dd, J=8, 1 Hz, 1H), 7.01 (t, J=8 Hz, 1H), 6.62 (d, J=8 Hz, 1H), 6.54-6.49 (m, 2H), 6.31 (d, J=9 Hz, 1H), 5.84 (dd, J=10, 5 Hz, 1H), 5.74 (br s, 1H), 5.32 (s, 1H), 5.27 (d, J=10 Hz, 1H), 4.33 (d, J=13 Hz, 1H), 4.26 (d, J=13 Hz, 1H), 3.86 (s, 3H), 3.76 (s, 3H), 3.74 (s, 3H), 3.65-3.57 (m, 2H), 3.42-3.32 (m, 1H), 3.26-3.18 (m, 2H), 3.02 (dd, J=15, 8 Hz, 1H), 2.72 (s, 3H), 2.70-2.56 (m, 3H), 2.34-2.25 (m, 2H), 2.13-1.98 (m, 7H), 1.85-1.78 (m, 1H), 1.67-1.60 (m, 1H), 1.56 (br s, 1H), 1.45-1.39 (m, 1H), 1.38-1.30 (m, 1H), 1.07 (t, J=7 Hz, 3H), 0.71 (t, J=7 Hz, 3H); ESI MS m/z 903 [M+H]$^+$.

Step 2: To a solution of 11'-(phenysulfanyl)vinorelbine (10 mg, 0.0113 mmol) in MeOH (0.1 mL) and Et$_2$O (2 mL) was added a solution of L-tartaric acid (10 mg, 0.067 mmol) in MeOH (0.1 mL) and Et$_2$O (1 mL). Collection of the precipitate by filtration gave 11'-(3-hydroxyphenysulfanyl)vinorelbine ditartrate (10.5 mg, 79%) as a white solid: mp 204-210° C. (dec); $^1$H NMR (500 MHz, CD$_3$OD) δ 8.03 (s, 1H), 7.44 (d, J=8 Hz, 1H), 7.31 (d, J=8 Hz, 1H), 7.03 (t, J=8 Hz, 1H), 6.65 (d, J=7 Hz, 1H), 6.66-6.30 (m, 2H), 6.41-6.35 (m, 2H), 6.90-6.84 (m, 2H), 5.36 (d, J=10 Hz, 1H), 5.30 (s, 1H), 4.90 (d, 1H), 4.66 (d, J=14 Hz, 1H), 4.43 (s, 4H), 4.11 (m, 1H), 3.88 (s, 3H), 3.79-3.67 (m, 8H), 3.63 (s, 1H), 3.50-3.42 (m, 1H), 3.14 (dd, J=15, 7 Hz, 1H), 2.95-2.83 (m, 3H), 2.75 (s, 3H), 2.65-2.52 (m, 2H), 2.19-2.05 (m, 3H), 2.03 (s, 3H), 1.96-1.85 (m, 2H), 1.68-1.59 (m, 1H), 1.42-1.33 (m, 1H), 1.12 (t, J=7 Hz, 3H), 0.71 (t, J=7 Hz, 3H); ESI MS m/z 903 [M+H]$^+$.

Example 19

Preparation of 11'-(3-Hydroxyethylsulfinyl)vinorelbine Trifluoroacetate

Hydrogen peroxide (30%, 10 μL, 0.35 mmol) was added dropwise to a solution of 11'-(2-hydroxyethylsulfanyl)vinorelbine (36.0 mg, 0.04 mmol) in CH$_3$CO$_2$H/H$_2$O (2:1, 1.5 mL) at 0° C. The reaction mixture was stirred at 0° C. for 10 min and then at room temperature for 1.5 h. The reaction mixture was poured slowly into saturated NaHCO$_3$ (30 mL) and then extracted with CH$_2$Cl$_2$ (60 mL). The organic layer was washed with brine, dried over Na$_2$SO$_4$, and concentrated. Purification by preparative TLC (silica gel, MeOH/CH$_2$Cl$_2$, 3:17) provided the two diasteromers of 11'-(2-hydroxyethylsulfinyl)vinorelbine as yellow solids (diasteromer 1: 6.8 mg, first to elute and diasteromer 2: 5.0 mg, 32%).

Diasteromer 1 (6.8 mg) was treated with CH$_2$Cl$_2$ (1 mL) and a drop of TFA. The solution was evaporated to give 11'-(2-hydroxyethylsulfinyl)vinorelbine trifluoroacetate as a yellow solid (8.9 mg, 97%): $^1$H NMR (300 MHz, CD$_3$OD) δ 10.70 (s, 1H), 8.01 (s, 1H), 7.53 (d, J=8.6 Hz, 1H), 7.43 (dd, J=8.6, 1.3 Hz, 1H), 6.64 (s, 1H), 6.32 (s, 1H), 5.83 (dd, J=10.7, 3.4 Hz, 1H), 5.80-5.79 (m, 1H), 5.55 (d, J=10.8 Hz, 1H), 5.21 (s, 1H), 4.85 (d, J=14.5 Hz, 1H), 4.63 (d, J=14.6 Hz, 1H), 4.03-3.63 (m, 10H), 3.79 (s, 3H), 3.72 (s, 3H), 3.66 (s, 3H), 3.37-3.32 (m, 1H), 3.00-3.29 (m, 3H), 2.79-2.72 (m, 1H), 2.70 (s, 3H), 2.60-2.51 (m, 1H), 2.24-2.17 (m, 1H), 2.10-2.03 (m, 3H), 1.97 (s, 3H), 1.92-1.89 (m, 1H), 1.61 (dd, J=14.4, 7.3 Hz, 1H), 1.41 (dd, J=14.2, 7.2 Hz, 1H), 1.04 (t, J=7.4 Hz, 3H), 0.60 (t, J=7.2 Hz, 3H); ESI MS m/z 871 [M+H]$^+$.

Example 20

Preparation of 11'-(3-Hydroxypropylsulfinyl)vinorelbine Trifluoroacetate

Hydrogen peroxide (30%, 10 μL, 0.35 mmol) was added dropwise to a solution of 11'-(3-hydroxypropylsulfanyl)vinorelbine (18.0 mg, 0.04 mmol) in CH$_3$CO$_2$H/H$_2$O (2:1, 1.5 mL) at 0° C. The reaction mixture was stirred at 0° C. for 10 min and then at room temperature for 1 h. The reaction mixture was poured slowly into saturated NaHCO$_3$ (30 mL) and the mixture was extracted with CH$_2$Cl$_2$ (60 mL). The organic layer was washed with brine, dried over Na$_2$SO$_4$, and concentrated. Purification by preparative TLC (silica gel, MeOH/EtOAc, 6:4) provided 11'-(3-hydroxypropylsulfinyl)vinorelbine as a yellow solid (12 mg, 67%). The solid was treated with CH$_2$Cl$_2$ (1 mL) and a drop of TFA. The solution was evaporated to give 11'-(3-hydroxypropylsulfinyl)vinorelbine trifluoroacetate as a yellow solid (14.7 mg, 98%): $^1$H NMR (300 MHz, CD$_3$OD) δ 10.81 (s, 1H), 8.09 (d, J=2.9 Hz, 1H), 7.63 (dd, J=8.6, 3.4 Hz, 1H), 7.52 (ddd, J=8.6, 1.6, 1.6 Hz, 1H), 6.75 (d, J=3.0 Hz, 1H), 6.43 (s, 1H), 5.94 (dd, J=10.4, 5.4 Hz, 1H), 5.93-5.88 (m, 1H), 5.67 (d, J=10.5 Hz, 1H), 5.32 (s, 1H), 4.97 (d, J=14.7, 7.1 Hz, 1H), 4.73 (dd, J=14.6, 2.8 Hz, 1H), 4.14-3.71 (m, 7H), 3.90 (s, 3H), 3.82 (s, 3H), 3.77 (s, 3H), 3.68-3.61 (m, 2H), 3.43 (d, J=15.8 Hz, 1H), 3.25-2.97 (m, 4H), 2.89-2.81 (m, 1H), 2.81 (s, 3H), 2.71-2.62 (m, 1H), 2.36-2.30 (m, 1H), 2.22-214 (m, 3H), 2.08 (s, 3H), 2.03-1.81 (m, 3H), 1.75-1.67 (m, 1H), 1.52 (dd, J=14.1, 6.7 Hz, 1H), 1.15 (t, J=7.4 Hz, 3H), 0.73-0.66 (m, 3H); ESI MS m/z 885 [M+H]$^+$.

Example 21

Preparation of 11'-Ethynylvinorelbine Ditartrate

Step 1: A solution of 11'-iodovinorelbine (550 mg, 0.608 mmol), in toluene (11 mL) and Et$_3$N (6 mL) was deoxygenated with argon Copper iodide (6 mg, 0.032 mmol) and PdCl$_2$(PPh$_3$)$_2$ (19 mg) were added and the mixture was purged again with argon. Trimethylsilylacetylene (0.13 mL, 0.917 mmol) was added and the mixture stirred at 55° C. overnight. The reaction mixture was cooled to room temperature, diluted with EtOAc (20 mL) and washed with saturated NH$_4$Cl (10 mL). The organic layer was dried (Na$_2$SO$_4$), filtered and concentrated. Purification by column chromatography (silica gel, MeOH/CH$_2$Cl$_2$, 4:96) gave 11'-(trimethylsilylethynyl)vinorelbine (400 mg), which was used directly in the next step.

Step 2: To a solution of 11'-(Trimethylsilylethynyl)vinorelbine (400 mg) in methanol (9 mL) was added potassium carbonate (catalyst) and the mixture was stirred at room temperature for 12 h. The solvent was removed under reduced pressure and the residue was taken up in CH$_2$Cl$_2$ (20 mL). The mixture was washed with H$_2$O (2×15 mL). The organic layer was dried (Na$_2$SO$_4$), filtered, and concentrated. Purification by column chromatography (silica gel, 0.5% to 4% MeOH, CH$_2$Cl$_2$, 0.1% Et$_3$N), followed by reverse phase chromatography (C18 column, H$_2$O/.CH$_3$CN, 0.1% TFA) gave 11'-ethynylvinorelbine trifluoroacetate (55 mg, 11%) as a dark yellow solid: mp 207-211° C.; $^1$H NMR (500 MHz, CD$_3$OD) δ 7.90 (s, 1H), 7.29 (d, J=8 Hz, 1H), 7.24 (dd, J=8, 1 Hz, 1H), 6.32 (s, 1H), 6.28 (s, 1H), 5.84 (dd, J=10, 4 Hz, 1H), 5.75 (d, J=5 Hz, 1H), 5.31 (s, 1H), 5.27 (d, J=10 Hz, 1H), 4.33 (d, J=13 Hz, 1H), 4.26 (d, J=13 Hz, 1H), 3.85 (s, 3H), 3.76 (s, 3H), 3.73 (s, 3H), 3.65 (d, J=17 Hz, 1H), 3.58 (s, 1H), 3.39-3.32 (m, 2H), 3.28-3.17 (m, 2H), 3.01 (dd, J=16, 8 Hz, 1H), 2.72 (s, 3H), 2.69-2.55 (m, 2H), 2.35-2.24 (m, 1H), 2.12-1.98 (m, 6H), 1.84-1.76 (m, 1H), 1.68-1.59 (m, 1H), 1.54 (br s, 1H), 1.37-1.28 (m, 1H), 1.09 (t, J=7 Hz, 3H), 0.69 (t, J=7 Hz, 3H); ESI MS m/z 803 [M+H]$^+$.

Step 3: To a solution of 11'-ethynylvinorelbine trifluoroacetate (83 mg, 0.103 mmol) in MeOH (0.2 mL) and Et$_2$O (3 mL) was added a solution of L-tartaric acid (16 mg, 0.106 mmol) in MeOH (0.2 mL) and Et$_2$O (1.5 mL). Collection of the precipitate by filtration gave 11'-ethynylvinorelbine ditartrate (74.2 mg, 65%) as an orange solid. mp 190° C. (dec). $^1$H NMR (500 MHz, CD$_3$OD) δ 7.99 (s, 1H), 7.37 (d, J=8 Hz, 1H), 7.29 (dd, J=8, 1 Hz, 1H), 6.41 (s, 1H), 6.36 (s, 1H), 5.88-5.81 (m, 2H), 5.37 (d, J=10 Hz, 1H), 5.29 (s, 1H), 4.90 (d, J=15 Hz, 1H), 4.65 (d, J=15 Hz, 1H), 4.39 (s, 4H), 4.15 (d, J=17 Hz, 1H), 3.88 (s, 3H), 3.77 (s, 3H), 3.76 (s, 3H), 3.75-3.68 (m, 2H), 3.62 (s, 1H), 3.47 (dd, J=16, 5 Hz, 1H), 3.36-3.33 (m, 2H), 3.13 (dd, J=16, 8 Hz, 1H), 2.97-2.89 (m, 2H), 2.86 (dd, J=14, 4 Hz, 1H), 2.75 (s, 3H), 2.67-2.55 (m, 2H), 2.18-2.09 (m, 3H), 2.03 (s, 3H), 1.96-1.85 (m, 2H), 1.68-1.59 (m, 1H), 1.42-1.33 (m, 1H), 1.13 (t, J=7 Hz, 3H), 0.71 (t, J=7 Hz, 3H); ESI MS m/z 803 [M+H]$^+$.

Example 22

Preparation of 11'-Hexynylvinorelbine

To a solution of 11'-iodovinorelbine (140 mg, 0.154 mmol) in THF (5 mL) was added triethylamine (1 mL), CuI (2.86 mg, 15 mmol) and (PPh$_3$)$_2$PdCl$_2$ (10.5 mg, 15 mmol) and the mixture deoxygenated with argon. 1-Hexyne (45 mg, 310 mmol) was added and the mixture was sealed and heated to 60° C. After 4 h, CuI (1.4 mg, 7 mmol), (PPh$_3$)$_2$PdCl$_2$ (5.5 mg, 8 mmol) and 1-hexyne (55 µL) were added and the mixture deoxygenated, sealed, and heated to 60° C. overnight. The mixture was diluted with dichloromethane, washed with water and brine, dried (Na$_2$SO$_4$), and concentrated under reduced pressure. Purification by flash chromatography (silica gel, eluent 2% methanol in dichloromethane containing 0.5% triethylamine) followed by reverse phase chromatography (C18 column, methanol/water) gave 11'-hexynylvinorelbine (18.8 mg, 14%). $^1$H NMR (300 MHz, CD$_3$OD) δ 7.77 (s, 1H), 7.26 (d, J=8 Hz, 1H), 7.15 (dd, J=8, 1 Hz, 1H), 6.35 (s, 1H), 6.26 (s, 1H), 5.83 (dd, J=10, 5 Hz, 1H), 5.90-5.78 (m, 1H), 5.30 (s, 1H), 5.22 (d, J=10 Hz, 1H), 4.12 (s, 2H), 4.42 (d, J=13 Hz, 1H), 4.39 (d, J=13 Hz, 1H), 3.85 (s, 3H), 3.76 (m, 1H), 3.75 (s, 3H), 3.73 (s, 3H), 3.57 (s, 1H), 3.43 (d, J=13 Hz, 1H), 3.39-3.27 (m, 1H), 3.20 (dt, J=9, 5 Hz, 1H), 3.06 (dd, J=16, 7 Hz, 1H), 2.71 (s, 3H), 2.65 (d, J=18 Hz, 1H), 2.58 (s, 1H), 2.50-2.48 (m, 3H), 2.38 (dt, J=9, 5 Hz, 1H), 2.14-2.00 (m, 3H), 2.01 (s, 3H), 1.90 (br s, 1H), 1.80 (m, 1H), 1.70-1.42 (m), 1.40-1.25 (m), 1.10 (t, J=7 Hz, 3H), 0.98 (t, J=7 Hz, 3H), 0.68 (t, J=7 Hz, 3H); ESI MS m/z 859 [M+H]$^+$.

Example 23

Preparation of 11'-(4-Methylpentynyl)vinorelbine

11'-Iodovinorelbine (53 mg, 0.058 mmol), copper(I) iodide (1.6 mg, 0.0088 mmol), dichlorobis(triphenylphosphine)palladium(II) (4.1 mg, 0.0059 mmol), toluene (1.2 mL), and triethylamine (0.8 mL) were combined in a resealable glass test tube. Argon was bubbled through the solution for 10 min. 4-Methyl-1-pentyne (41.3 mg, 0.351 mmol) was added, the test tube sealed, and the mixture was heated at 55° C. for 1.5 h. Saturated NaHCO$_3$ (5 mL) was added and the mixture was extracted with ethyl acetate (3×5 mL). The combined organic extracts were washed with brine (5 mL), dried over MgSO$_4$, and evaporated to dryness in vacuo. The residue was purified by prep TLC (silica gel, methylene chloride/methanol, 95/5) to provide 11'-(4-methylpentynyl)vinorelbine (9 mg, 18% yield) as a white powder: $^1$H NMR (500 MHz, CD$_3$OD) δ 7.76 (s, 1H), 7.25 (d, J=8.5 Hz, 1H), 7.15 (dd, J=8.5, 1.5 Hz, 1H), 6.32 (s, 1H), 6.26 (s, 1H), 5.87-5.82 (m, 1H), 5.76 (d, J=4.0 Hz, 1H), 5.30 (s, 1H), 5.26 (d, J=10.0 Hz, 1H), 4.89-4.79 (m, 1H), 4.35 (br s, 2H), 3.85 (s, 3H), 3.75-3.65 (m, 7H), 3.57 (s, 1H), 3.45-3.28 (m, 2H), 3.23-3.15 (m, 2H), 3.06-2.99 (m, 1H), 2.71 (s, 3H), 2.68-2.54 (m, 3H), 2.40-2.23 (m, 4H), 2.12-2.02 (m, 9H), 1.93-1.77 (m, 2H), 1.66-1.57 (m, 2H), 1.35-1.28 (m, 2H), 1.11-1.06 (m, 9H), 0.69 (t, J=7.5 Hz, 3H); ESI MS m/z 859 [M+H]$^+$.

Example 24

Preparation of 11'-(3-Methoxypropynyl)vinorelbine Trifluoroacetate

11'-Iodovinorelbine (68 mg, 0.075 mmol), copper(I) iodide (2.1 mg, 0.011 mmol), dichlorobis(triphenylphosphine)palladium(II), (5.3 mg, 0.008 mmol) toluene (1.2 mL), and triethylamine (0.8 mL) were combined in a resealable glass test tube. Argon was bubbled through the solution for 30 min. Methyl propargyl ether (32 mg, 0.451 mmol) was added, the test tube sealed, and the mixture was heated at 55° C. for 1.5 h. Saturated NaHCO$_3$ (5 mL) was added and the mixture was extracted with ethyl acetate (3×5 mL). The combined organic extracts were washed with brine (5 mL), dried over MgSO$_4$, and evaporated to dryness in vacuo. The residue was purified by reverse phase chromatography (C18, acetonitrile/water, 0.05% TFA) to provide 11'-(3-methoxypropynyl)vinorelbine trifluoroacetate (8.3 mg, 10% yield) as a white powder after lyophilization: $^1$H NMR (500 MHz, CD$_3$OD) δ 10.40 (bs, 1H), 7.86 (s, 1H), 7.35 (d, J=8.4 Hz, 1H), 7.23 (dd, J=8.4, 1.3 Hz, 1H), 6.64 (s, 1H), 6.41 (s, 1H), 5.93 (dd, J=10.4, 5.4 Hz, 1H), 5.87 (d, J=3.7 Hz, 1H), 5.63 (d, J=10.4 Hz, 1H), 5.30 (s, 1H), 4.87 (m, 1H), 4.60 (d, J=14.5 Hz, 1H), 4.32 (s, 2H), 4.07 (d, J=17.0 Hz, 1H), 3.96-3.71 (m, 4H), 3.88 (s, 3H), 3.81 (s, 3H), 3.76 (s, 3H), 3.71 (s, 1H), 3.43 (s, 3H) 3.42 (m, 1H), 3.11 (m, 2H), 2.81 (m, 1H), 2.79 (s, 3H), 2.61 (m, 1H), 2.31 (m, 1H), 2.15 (q, J=7.4 Hz, 2H), 2.09 (m, 2H), 2.06 (s, 3H), 1.98 (m, 1H), 1.69 (m, 1H), 1.47 (m, 1H), 1.14 (t, J=7.5 Hz, 3H), 0.70 (t, J=7.2 Hz, 3H); ESI MS m/z 847 [M+H]$^+$.

Example 25

Preparation of 11'-Cyanovinorelbine Ditartrate

Step 1: A mixture of tris(dibenzylideneacetone)dipalladium(0) (21 mg, 0.0232 mmol), 1,1'-bis(diphenylphosphino) ferrocene (26 mg, 0.0464 mmol), Zn(CN)$_2$ (54 mg, 0.46 mmol) in DMF (1.0 mL) was deoxygenated with argon a solution of 11'-iodovinorelbine (210 mg, 0.23 mmol) in DMF (7 mL) was added and the mixture was purged again with argon. The reaction mixture was heated at 65° C. for 3.5 h, then cooled to 25° C. and diluted with EtOAc. The organic layer was washed with 5% LiCl, brine, dried (Na$_2$SO$_4$), and concentrated. Purification by reverse phase chromatography (C8, CH$_3$CN/H$_2$O, 0.05% NH$_4$OH) gave 11'-cyanovinorelbine (15.3 mg, 8%). $^1$H NMR (500 MHz, MeOD) δ 8.18 (s, 1H), 7.49 (d, J=9 Hz, 1H), 7.40 (d, J=9 Hz, 1H), 6.32 (s, 1H), 6.27 (s, 1H), 5.83 (dd, J=10, 4 Hz, 1H), 5.76 (d, J=4 Hz, 1H), 5.29 (s, 1H), 5.27 (s, 1H), 4.37 (s, 2H), 3.85 (s, 3H), 3.75 (s, 3H), 3.74 (s, 3H), 3.58 (s, 3H), 3.20 (dt, J=9, 5 Hz, 1H), 3.00 (dd, J=16, 8 Hz, 1H), 2.72 (s, 3H), 2.70-2.58 (m, 3H), 2.38 (dd, J=14, 8 Hz, 1H), 2.30 (dt, J=11, 6 Hz, 1H), 2.07-2.01 (m, 6H), 1.77 (m, 1H), 1.61 (m, 2H), 1.34 (m, 4H), 1.09 (t, J=7 Hz, 3H), 0.67 (t, J=7 Hz, 3H); ESI MS m/z 804 [M+H]$^+$.

Step 2: 11'-Cyanovinorelbine (68 mg, 0.075 mmol) in methylene chloride (1 mL) was treated with a solution of L-tartaric acid (22.5 mg, 0.150 mmol) in methanol (0.20 mL). After 4 hours, reaction mixture was reduced to dryness. The residue was lyophilized with water and acetonitrile to provide 11'-cyanovinorelbine ditartrate (80 mg, 96% yield) as a white powder: $^1$H NMR (500 MHz, CD$_3$OD) δ 8.26 (br s, 1H), 7.57 (d, J=8.5 Hz, 1H), 7.48 (d, J=8.5 Hz, 1H), 6.35 (s, 1H), 6.27-6.25 (m, 1H), 5.88-5.84 (m, 2H), 5.33 (d, J=10.5 Hz, 1H), 5.28 (s, 1H), 4.77-4.71 (m, 1H), 4.42 (s, 4H), 4.17-4.10 (m, 1H), 3.88-3.82 (m, 4H), 3.78-3.72 (m, 7H), 3.68-3.61 (m, 2H), 3.44-3.43 (m, 1H), 3.39-3.30 (m, 1H), 3.17-3.11 (m, 2H), 2.92-2.88 (m, 1H), 2.76-2.71 (m, 5H), 2.68-2.60 (m, 1H), 2.43-2.40 (m, 1H), 2.18-2.07 (m, 3H), 2.02 (s, 3H), 1.99-1.94 (m, 1H), 1.82-1.76 (m, 1H), 1.64-1.60 (m, 1H), 1.41-1.29 (m, 2H), 1.14 (t, J=7.5 Hz, 3H), 0.66 (t, J=7.5 Hz, 3H); ESI MS m/z 804 [M+H]$^+$.

Example 26

Preparation of 11'-Acetylvinorelbine Ditartrate

11'-(Trimethylsilanylethynyl)vinorelbine (320 mg, 0.365 mmol) was added to an ice-water cold solution of CH$_2$Cl$_2$ (10 mL) and TFA (10 mL), and the reaction mixture was stirred at room temperature. After 20 min, the reaction was quenched by the addition of saturated NaHCO$_3$, and the pH was adjusted to 8 using 3 N NaOH and saturated NaHCO$_3$. The resulting suspension was extracted with EtOAc (250 mL). The organic solution was washed with water and brine, then dried (Na$_2$SO$_4$) and evaporated to dryness under vacuum. Purification by column chromatography (silica gel, 95.5:4:0.5 CH$_2$Cl$_2$/MeOH/Et$_3$N) followed by reverse phase chromatography (C18, acetonitrile/water, 0.05% TFA) gave the product as the TFA salt. After conversion to the free base, treatment with 2 equivalents of L-tartaric acid gave 11'-acetylvinorelbine L-tartaric acid salt as a white solid: $^1$H NMR (500 MHz, CD$_3$OD) 8.57 (d, J=1.0 Hz, 1H), 7.88 (dd, J=8.5, 1.5 Hz, 1H), 7.48 (d, J=8.5 Hz, 1H), 6.41 (s, 1H), 6.37 (s, 1H), 5.88-5.83 (m, 2H), 5.38 (d, J=10.0 Hz, 1H), 5.29 (s, 1H), 5.03 (d, J=15.0 Hz, 1H), 4.71 (d, J=14.5 Hz, 1H), 4.40 (s, 4H), 4.14 (d, J=17.0 Hz, 1H), 3.88 (s, 3H), 3.78-3.74 (m, 8H), 3.63 (s, 1H), 3.46 (dd, J=15, 4.5 Hz, 1H), 3.27-3.32 (m, 1H), 3.14 (dd, J=16.0, 8.0 Hz, 1H), 2.96 (s, 1H), 2.92-2.86 (m, 2H), 2.75 (s, 3H), 2.70 (s, 3H), 2.64 (dd, J=15.5, 12.0 Hz, 1H), 2.18-2.09 (m, 3H), 2.03 (s, 4H), 1.95-1.86 (m, 2H), 1.66-1.61 (m, 1H), 1.42-1.37 (m, 1H), 1.15 (t, J=7.5 Hz, 3H), 0.69 (t, J=7.5 Hz, 3H); ESI MS m/z 821 [M+H]$^+$.

Example 27

Preparation of 11'-(Methoxycarbonyl)vinorelbine Trifluoroacetate

Carbon monoxide was bubbled through a solution of 11'-iodovinorelbine (30 mg, 0.033 mmol), triethylamine (33 mg, 0.331 mmol) and bis(triphenylphosphine)palladium(II) dichloride (4.6 mg, 0.007 mmol) in a mixture of DMF/methanol (2 mL, 1:1) for 5 min. The reaction mixture was heated at 50° C. for 12 h under one atmosphere of carbon monoxide (balloon). The solution was diluted with ethyl acetate (20 mL) then washed with satd NaHCO$_3$ (2×5 mL) and brine (5 mL), dried over MgSO$_4$, and evaporated to dryness in vacuo. The residue was purified by reverse phase chromatography (C18, acetonitrile/water, 0.05% TFA) to provide 11'-(methoxycarbonyl)vinorelbine trifluoroacetate (10 mg, 28% yield) as a white powder after lyophilization: $^1$H NMR (500 MHz, CD$_3$OD) δ 10.64 (bs, 1H), 8.50 (s, 1H), 7.85 (dd, J=8.6, 1.4 Hz, 1H), 7.44 (d, J=8.6 Hz, 1H), 6.66 (s, 1H), 6.41 (s, 1H), 5.92 (dd, J=10.4, 5.2 Hz, 1H), 5.88 (m, 1H), 5.63 (d, J=10.6 Hz, 1H), 5.31 (s, 1H), 4.95 (d, J=14.6 Hz, 1H), 4.71 (d, J=14.5 Hz, 1H), 4.09 (d, J=17.0 Hz, 1H), 3.89 (d, J=14.2 Hz, 1H), 3.91-3.69 (m, 5H), 3.91 (s, 3H), 3.88 (s, 3H), 3.81 (s, 3H), 3.77 (s, 3H), 3.37 (d, J=14.5 Hz, 1H), 3.13 (m, 2H), 2.84 (dd, J=13.3, 4.2 Hz, 1H), 2.79 (s, 3H), 2.65 (m, 1H), 2.29 (m, 1H), 2.17 (q, J=7.3 Hz, 2H), 2.08 (m, 1H), 2.06 (s, 3H), 1.94 (m, 1H), 1.69 (m, 1H), 1.47 (m, 1H), 1.14 (t, J=7.5 Hz, 3H), 0.69 (t, J=7.3 Hz, 3H); ESI MS m/z 837 [M+H]$^+$.

Example 28

Preparation of 11'-(2,2,2-Trichloroethoxycarbonyl)vinorelbine

Carbon monoxide was bubbled through a solution of 11'-iodovinorelbine (151 mg, 0.167 mmol), triethylamine (169 mg, 1.67 mmol) and bis(triphenylphosphine)palladium(II) dichloride (23 mg, 0.033 mmol) in a mixture of DMF/2,2,2-trichloroethanol (4 mL, 1:1) for 5 min. The reaction mixture was heated at 50° C. for 14 h under one atmosphere of carbon monoxide (balloon). The solution was diluted with ethyl acetate (35 mL) then washed with saturated NaHCO$_3$ (2×20 mL) and brine (20 mL), dried over MgSO$_4$, and evaporated to dryness in vacuo. The residue was purified by reverse phase chromatography (C18, acetonitrile/water, 0.05% TFA) to provide 11'-(2,2,2-trichloroethoxycarbonyl)vinorelbine Trifluoroacetate (78 mg, 40% yield) as a white powder after lyophilization: $^1$H NMR (500 MHz, CD$_3$OD) δ 8.62 (s, 1H), 7.97 (dd, J=8.7, 1.5 Hz, 1H), 7.52 (d, J=8.7 Hz, 1H), 6.37 (s, 2H), 5.87 (m, 2H), 5.39 (d, J=10.1 Hz, 1H), 5.30 (s, 1H), 5.11 (d, J=12.2 Hz, 1H), 5.07 (d, J=12.1 Hz, 1H), 4.98 (d, J=14.7 Hz, 1H), 4.74 (d, J=14.7 Hz, 1H), 4.09 (m, 1H), 3.92-3.72 (m, 5H), 3.88 (s, 3H), 3.77 (s, 3H), 3.76 (s, 3H), 3.63 (s, 1H), 3.48 (m, 1H), 3.33 (m, 1H), 3.16 (m, 1H), 2.88 (dd, J=13.5, 4.6 Hz, 1H), 2.75 (s, 3H), 2.64 (dd, J=15.4, 12.5 Hz, 1H), 2.16 (q, J=7.4 Hz, 2H), 2.12 (m, 1H), 2.03 (s, 3H), 1.98 (m, 1H), 1.87 (m, 1H), 1.64 (m, 1H), 1.40 (m, 1H), 1.14 (t, J=7.5 Hz, 3H), 0.69 (t, J=7.3 Hz, 3H); ESI MS m/z 953 [M+H]$^+$.

Example 29

Preparation of 11'-(2,2-dichloroethoxycarbonyl)vinorelbine Trifluoroacetate

The second eluting fraction formed during the preparation of 11'-carboxyvinorelbine (see Example 33) was purified by reverse phase chromatography (C18, acetonitrile/water, 0.05% TFA) to provide 111'-(2,2-dichloroethoxycarbonyl)vinorelbine trifluoroacetate (2.4 mg, 3.5% yield) as a white powder after lyophilization: $^1$H NMR (500 MHz, CD$_3$OD) δ 10.71 (bs, 1H), 8.55 (s, 1H), 7.90 (dd, J=8.6, 1.4 Hz, 1H), 7.48 (d, J=8.7 Hz, 1H), 6.63 (s, 1H), 6.41 (s, 1H), 5.91 (dd, J=10.4, 4.7 Hz, 1H), 5.88 (d, J=4.2 Hz, 1H), 5.61 (d, J=10.0 Hz, 1H), 5.31 (s, 1H), 4.97 (d, J=14.7 Hz, 1H), 4.73 (m, 3H), 4.09 (d, J=17.0 Hz, 1H), 3.95 (d, J=13.3 Hz, 1H), 3.89 (s, 3H), 3.86-3.74 (m, 2H), 3.81 (s, 3H), 3.77 (s, 3H), 3.71 (s, 1H), 3.66 (m, 2H), 3.33 (m, 1H), 3.09 (m, 3H), 2.85 (dd, J=13.5, 4.2 Hz, 1H), 2.78 (s, 3H), 2.65 (m, 1H), 2.28 (m, 1H), 2.17 (q, J=7.4 Hz, 2H), 2.10 (m, 1H), 2.06 (s, 3H), 1.96 (m, 1H), 1.69 (m, 1H), 1.47 (m, 1H), 1.14 (t, J=7.5 Hz, 3H), 0.69 (t, J=7.3 Hz, 3H); ESI MS m/z 919 [M+H]$^+$.

Example 30

Preparation of 11'-Phenylvinorelbine Trifluoroacetate

To a solution of 11'-iodovinorelbine (38 mg, 0.04 mmol) in dioxane (1 mL) was added phenylboronic acid (10 mg, 0.08 mmol) and Cs$_2$CO$_3$ (68 mg, 0.21 mmol). The mixture was deoxygenated with an argon purge, and [1,1'-bis(diphenylphospino)ferrocene]dichloropalladium (5 mg, 0.006 mmol) was added. The resulting mixture was deoxygenated again and then heated to 60° C. for 2 h. The reaction mixture was cooled to room temperature, diluted with CH$_2$Cl$_2$, and filtered through Celite. The filtrate was washed with water and brine, and then dried (MgSO$_4$). Purification by column chromatography (silica gel, CH$_2$Cl$_2$/MeOH, 9:1) followed by prep-TLC (silica gel, EtOAc/MeOH, 7:3) gave 11'-phenylvinorelbine (9 mg, 26%). The solid was dissolved in CH$_2$Cl$_2$ (1 mL) and treated with a drop of TFA. The solution was evaporated to give 11'-phenylvinorelbine trifluoroacetate (11.3 mg, quantitative): $^1$H NMR (300 MHz, CD$_3$OD) δ 10.1 (s, 1H), 7.89 (s, 1H), 7.58-7.56 (m, 2H), 7.36 (s, 2H), 7.31 (dd, J=7.3, 6.9 Hz, 2H), 7.21-7.16 (m, 1H), 6.55 (s, 1H), 6.33 (s, 1H), 5.85-5.77 (m, 2H), 5.55 (d, J=11.1 Hz, 1H), 5.22 (s, 1H), 4.93 (d, J=14.5 Hz, 1H), 4.59 (d, J=14.4 Hz, 1H), 3.99 (d, J=17.1 Hz, 1H), 3.85-3.63 (m, 6H), 3.80 (s, 3H), 3.71 (s, 3H), 3.68 (s, 3H), 3.35 (d, J=15.3 Hz, 1H), 3.14-2.99 (m, 2H), 2.77-2.69 (m, 1H), 2.69 (s, 3H), 2.54 (dd, J=14.3, 12.1 Hz, 1H), 2.25-2.18 (m, 1H), 2.10-2.03 (m, 3H), 1.97 (s, 3H), 1.89-1.84 (m, 1H), 1.63 (dd, J=14.6, 7.5 Hz, 1H), 1.38 (dd, J=14.5, 7.2 Hz, 1H), 1.04 (t, J=7.4 Hz, 3H), 0.67 (t, J=7.2 Hz, 3H); ESI MS m/z 855 [M+H]$^+$.

Example 31

Preparation of 11'-(3-Hydroxyphenyl)vinorelbine Trifluoroacetate

To a solution of 11'-iodovinorelbine (87 mg, 0.10 mmol) in dioxane (1 mL) was added 3-hydroxyphenylboronic acid (27 mg, 0.19 mmol) and Cs$_2$CO$_3$ (157 mg, 0.480 mmol). The mixture was deoxygenated with argon, and PdCl$_2$(dppf)$_2$ (8 mg, 0.01 mmol) was added. The resulting mixture was deoxygenated with argon again and then heated to 60° C. for 7 h and then to 70° C. overnight. The reaction mixture was cooled to room temperature, diluted with CH$_2$Cl$_2$, and filtered through Celite. The filtrate was washed with water and brine, dried (Na$_2$SO$_4$), and the solvent evaporated in vacuo. Purification by column chromatography (silica gel, CH$_2$Cl$_2$/MeOH, 9:1), followed by reverse phase chromatography (C18, acetonitrile/water, 0.05% TFA) gave 11'-(3-hydroxyphenyl)vinorelbine trifluoroacetate (5 mg, 4.5%) as a white solid after lyophilization: $^1$H NMR (500 MHz, CD$_3$OD) δ 7.96 (s, 1H), 7.49-7.47 (m, 2H), 7.23 (t, J=8.0 Hz, 1H), 7.14 (d, J=7.5 Hz, 1H), 7.09-7.08 (m, 1H), 6.74 (dd, J=8.0, 1.5 Hz, 1H), 6.56-6.50 (m, 1H), 6.44 (s, 1H), 5.94-5.89 (m, 2H), 5.60 (d, J=11.0 Hz, 1H), 5.34 (s, 1H), 5.03-5.00 (m, 1H), 4.76-4.73 (m, 1H), 4.08 (d, J=16.5 Hz, 1H), 3.90-3.72 (m, 10H), 3.56-3.52 (m, 2H), 3.45-3.38 (m, 2H), 3.18-3.03 (m, 3H), 2.91-2.87 (m, 1H), 2.78 (s, 3H), 4.70-4.63 (m, 1H), 2.39-2.34 (m, 1H), 2.19-2.14 (m, 2H), 2.07-1.96 (m, 5H), 1.77-1.72 (m, 1H), 1.48-1.43 (m, 1H), 1.06-1.11 (m, 4H), 0.78-0.75 (m, 3H); ESI MS m/z 871 [M+H]$^+$.

Example 32

Preparation of 11'-(3,5-Dimethylisoxazol-4-yl)vinorelbine Trifluoroacetate

To a solution of 11'-iodovinorelbine (72 mg, 0.08 mmol) in dioxane (1 mL) was added 3,5-dimethylisoxazole-4-boronic acid (22 mg, 0.16 mmol) and Cs$_2$CO$_3$ (130 mg, 0.4 mmol). The mixture was deoxygenated with an argon purge, and [1,1'-bis(diphenylphospino)ferrocene]dichloropalladium ((4 mg, 0.005 mmol) was added. The resulting mixture was deoxygenated again and then heated to 60° C. for 7 h. The reaction mixture was cooled to room temperature, diluted with CH$_2$Cl$_2$, and filtered through Celite. The filtrate was washed with water and brine, and then dried (MgSO$_4$). Purification by column chromatography (silica gel, CH$_2$Cl$_2$/MeOH, 9:1) followed by prep-TLC (silica gel, CH$_2$Cl$_2$/MeOH 9:1) gave 11'-(3,5-dimethylisoxazol-4-yl)vinorelbine (14 mg, 20%). The solid was dissolved in CH$_2$Cl$_2$ (1 mL) and treated with a drop of TFA. The solution was evaporated to give 11'-(3,5-dimethylisoxazol-4-yl)vinorelbine trifluoroacetate (17.6 mg, 90%): $^1$H NMR (300 MHz, CD$_3$OD) δ 10.2 (s, 1H), 7.56 (s, 1H), 7.38 (d, J=8.4 Hz, 1H), 7.01 (dd, J=8.4, 1.4 Hz, 1H), 6.66 (s, 1H), 6.32 (s, 1H), 5.85-5.77 (m, 2H), 5.56 (d, J=9.8 Hz, 1H), 5.22 (s, 1H), 4.85 (d, J=14.6 Hz, 1H), 4.59 (d, J=14.5 Hz, 1H), 4.00-3.85 (m, 2H), 3.80-3.62 (m, 5H), 3.80 (s, 3H), 3.71 (s, 3H), 3.67 (s, 3H), 3.34 (d, J=15.7 Hz, 1H), 3.15-2.98 (m, 2H), 2.75-2.70 (m, 1H), 2.70 (s, 3H), 2.54 (dd, J=15.5, 12.2 Hz, 1H), 2.30 (s, 3H), 2.25-2.17 (m, 1H), 2.15 (s, 3H), 2.10-2.02 (m, 3H), 1.97 (s, 3H), 1.86-1.84 (m, 1H), 1.59 (dd, J=14.5, 7.4 Hz, 1H), 1.40 (dd, J=14.5, 7.3 Hz, 1H), 1.04 (t, J=7.4 Hz, 3H), 0.64 (t, J=7.2 Hz, 3H); ESI MS m/z 874 [M+H]$^+$.

Example 33

Preparation of 3,11'-Dimethylvinorelbine Trifluoroacetate

Dimethylzinc (2.0 M in toluene, 0.16 mL, 0.32 mmol) was added to 11'-iodovinorelbine (148 mg, 0.16 mmol) and [1,1'-bis(diphenylphosphino)ferrocene]dichloropalladium(II) (13 mg, 0.016 mmol) in anhydrous 1,4-dioxane (3 mL) under nitrogen. The reaction mixture was heated at 45° C. for 10 h then quenched by the addition of saturated NaHCO$_3$ (8 mL). After extraction with chloroform (3×10 mL) the combined organic extracts were washed with brine (5 mL), dried over MgSO$_4$, and evaporated to dryness in vacuo. The residue was initially purified by reverse phase chromatography (C18, acetonitrile/water, 0.05% TFA) to provide two separate products. Purification of the first fraction by reverse phase chromatography (C18, acetonitrile/water, 0.05% TFA) gave 3,11'-dimethylvinorelbine trifluoroacetate (16.0 mg, 9.5% yield) as a white powder after lyophilization; $^1$H NMR (500 MHz, CD$_3$OD) δ 10.3 (bs, 1H), 7.58 (s, 1H), 7.37 (d, J=8.4 Hz, 1H), 7.09 (d, J=8.4 Hz, 1H), 6.49 (s, 1H), 6.44 (s, 1H), 5.95 (dd, J=10.5, 4.2 Hz, 1H), 5.88 (d, J=4.2 Hz, 1H), 5.63 (d, J=10.4 Hz, 1H), 5.31 (s, 1H), 5.01 (d, J=14.7 Hz, 1H), 4.75 (d, J=14.7 Hz, 1H), 4.16 (d, J=16.6 Hz, 1H), 4.08 (d, J=16.6 Hz, 1H), 3.96 (dd, J=15.7, 5.5 Hz, 1H), 3.88-3.75 (m, 3H), 3.88 (s, 3H), 3.82 (s, 3H), 3.75 (s, 3H), 3.66 (s, 1H), 3.61 (d, J=13.0 Hz, 1H), 3.46 (d, J=15.7 Hz, 1H), 3.18 (m, 2H), 3.06 (s, 3H), 2.96 (dd, J=13.0, 4.5 Hz, 1H), 2.79 (s, 3H), 2.63 (dd, J=15.7, 12.1 Hz, 1H), 2.38 (m, 1H), 2.17 (q, J=7.5 Hz, 2H), 2.08 (m, 1H), 2.07 (s, 3H), 1.98 (m, 1H), 1.74 (m, 1H), 1.46 (m, 1H), 1.16 (t, J=7.4 Hz, 3H), 0.78 (t, J=7.3 Hz, 3H); ESI MS m/z 807 [M+H]$^+$

Example 34

Preparation of 3-Methyl-11'-iodovinorelbine Trifluoroacetate

The second eluting fraction formed during the preparation of 3,11'-dimethylvinorelbine (see Example 53) was purified by reverse phase chromatography (C18, acetonitrile/water, 0.05% TFA) to give 3-methyl-11'-iodovinorelbine trifluoroacetate (8.8 mg, 4.7% yield); $^1$H NMR (500 MHz, CD$_3$OD) δ 8.20 (s, 1H), 7.52 (dd, J=8.6, 1.3 Hz, 1H), 7.31 (d, J=8.6 Hz, 1H), 6.46 (m, 1H), 6.44 (s, 1H), 5.94 (dd, J=10.5, 4.2 Hz, 1H), 5.88 (d, J=4.4 Hz, 1H), 5.63 (d, J=10.7 Hz, 1H), 5.31 (s, 1H), 5.00 (d, J=14.8 Hz, 1H), 4.74 (d, J=16.5 Hz, 1H), 4.17 (d, J=16.4 Hz, 1H), 4.05 (d, J=16.5 Hz, 1H), 3.95 (dd, J=15.8, 5.4 Hz, 1H), 3.87-3.75 (m, 3H), 3.88 (s, 3H), 3.82 (s, 3H), 3.76 (s, 3H), 3.67 (s, 1H), 3.58 (d, J=13.3 Hz, 1H), 3.47 (d, J=15.9 Hz, 1H), 3.18 (m, 2H), 3.06 (s, 3H), 2.96 (dd, J=13.1, 8.6 Hz, 1H), 2.79 (s, 3H), 2.64 (m, 1H), 2.38 (m, 1H), 2.17 (q, J=7.3 Hz, 2H), 2.08 (m, 1H), 2.07 (s, 3H), 1.98 (m, 1H), 1.73 (m, 1H), 1.46 (m, 1H), 1.16 (t, J=7.5 Hz, 3H), 0.75 (t, J=7.3 Hz, 3H); ESI MS m/z 919 [M+H]$^+$.

Example 35

Preparation of 11'-Aminovinorelbine Trifluoroacetate

11'-Aminovinorelbine was prepared according to the scheme below.

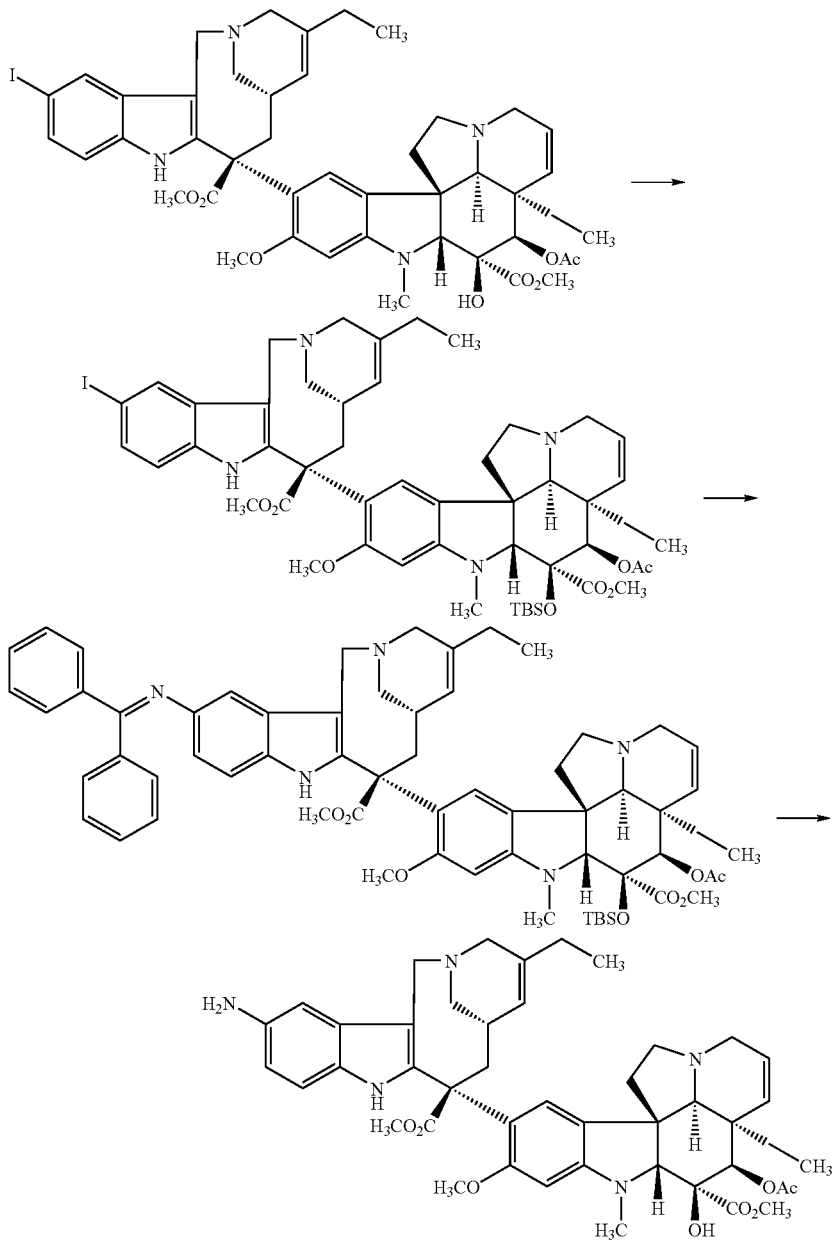

Step 1: A solution of 11'-iodovinorelbine (211 mg, 0.233 mmol) in $CH_2Cl_2$ (5 mL) was charged with N,N-diisopropylethylamine (0.41 g, 2.33 mmol) and tert-butyldimethylsilyl trifluoromethanesulfonate (123 mg, 0.466 mmol). After 1 h, the reaction mixture was diluted with ethyl acetate (30 mL), then washed with saturated $NaHCO_3$ (2×10 mL) and brine (10 mL). The solution was dried ($MgSO_4$) and concentrated to a brown solid which was purified by flash chromatography (silica gel, 20:79:1 to 50:49:1 ethyl acetate/hexanes/triethylamine) to yield 11'-iodo-3-(tert-butyldimethylsilanyloxy)vinorelbine (180 mg, 76%) as a white solid: ESI MS m/z 1019 $[M+H]^+$.

Step 2: 11'-Iodo-3-(tert-butyldimethylsilanyloxy)vinorelbine (172 mg, 0.169 mmol), benzophenone imine (71 μL, 0.42 mmol), and NaOt-Bu (48 mg, 0.50 mmol) were dissolved in anhydrous toluene (1.5 mL) while stirring under argon atmosphere in a resealable tube. The mixture was deoxygenated with argon at room temperature for 3 min then tris(dibenzylideneacetone)dipalladium(0) (15.5 mg, 16.9 μmol) and 2-(dicyclohexylphosphino)-2',4',6'-tri-1-propyl-1,1'-biphenyl (16.1 mg, 33.9 μmol) were added. The reaction vessel was sealed and the mixture heated to 80° C. for 4 h. The reaction mixture was cooled to room temperature, diluted with EtOAc, filtered through diatomaceous earth, and concentrated to provide crude 12'-benzhydrylidene-amino-3-(tert-butyldimethylsilanyloxy)vinorelbine: ESI MS m/z 1072 [M+H]$^+$.

Step 3: A solution of crude 12'-benzhydrylideneamino-3-(tert-butyldimethylsilanyloxy)vinorelbine (181 mg, 0.17 mmol) in methanol (1.0 mL) was treated with NaOAc (123 mg, 1.50 mmol) and hydroxylamine hydrochloride (81 mg, 1.1 mmol). After 6 h, the reaction mixture was concentrated to dryness. The residue was diluted with saturated NaHCO$_3$ (10 mL) and extracted with CH$_2$Cl$_2$ (2×10 mL). The combined extracts were dried (Na$_2$SO$_4$), concentrated, and purified by reverse phase chromatography (C18, acetonitrile/water, 0.05% TFA) to provide 11'-amino-3-(tert-butyldimethylsilanyloxy)vinorelbine trifluoroacetate (25 mg, 16% yield) as a white powder after lyophilization: ESI MS m/z 908 [M+H]$^+$.

Step 4: A solution of 11'-amino-3-(tert-butyldimethylsilanyloxy)vinorelbine trifluoroacetate (20 mg, 0.17 mmol) in THF (1.0 mL) was treated with Bu$_4$NF (80 μL of a 1 N solution in THF, 0.080 mmol). After 3 h, the reaction appeared complete as indicated by ESI mass spectral analysis. The reaction was diluted with saturated NaHCO$_3$ (10 mL) and extracted with CH$_2$Cl$_2$ (2×10 mL). The combined extracts were dried (Na$_2$SO$_4$) and then concentrated. The residue was purified by reverse phase chromatography (C18, acetonitrile/water, 0.05% TFA) to provide 11'-aminovinorelbine trifluoroacetate (15 mg, 75% yield) as a white powder after lyophilization: $^1$H NMR (500 MHz, CD$_3$OD) δ 10.73 (br s, 1H), 7.66 (d, J=2.0 Hz, 1H), 7.51 (d, J=9 Hz, 1H), 7.11 (dd, J=8.5, 2.0 Hz, 1H), 6.72 (s, 1H), 6.40 (s, 1H), 5.93-5.88 (m, 2H), 5.65 (d, J=10.5 Hz, 1H), 5.29 (s, 1H), 4.81-4.79 (m, 1H), 4.72-4.70 (m, 1H), 4.13-4.07 (m, 2H), 3.93-3.88 (m, 4H), 3.82-3.80 (m, 4H), 3.78-3.70 (m, 7H), 3.38-3.32 (m, 1H), 3.17-3.08 (m, 2H), 2.86-2.80 (m, 4H), 2.65-2.59 (m, 1H), 2.32-2.26 (m, 1H), 2.19-2.12 (m, 3H), 2.06 (s, 3H), 1.99-1.94 (m, 1H), 1.64-1.65 (m, 1H), 1.52-1.48 (m, 1H), 1.44 (t, J=7.5 Hz, 3H), 0.65 (t, J=7.5 Hz, 3H); ESI MS m/z 794 [M+H]$^+$.

Example 36

Preparation of 11'-(4-Methoxyphenylamino)vinorelbine Trifluoroacetate

Step 1: 11'-Iodo-3-(tert-butyldimethylsilanyloxy)vinorelbine (52.6 mg, 0.0522 mmol), p-anisidine (15 mg, 0.13 mmol), and NaOt-Bu (16 mg, 0.16 mmol) were dissolved in anhydrous toluene (1.5 mL) while stirring under argon atmosphere in a resealable tube. The reaction mixture was deoxygenated with an argon purge at room temperature for 3 min then tris(dibenzylideneacetone)dipalladium(0) (4.7 mg, 5.2 μmol) and 2-(dicyclohexylphosphino)-2',4',6'-tri-isopropyl-1,1'-biphenyl (4.9 mg, 10 μmol) were added. The reaction vessel was sealed and the mixture heated to 80° C. for 4 h. The reaction mixture was cooled to room temperature, diluted with EtOAc, filtered through diatomaceous earth, and then concentrated to provide crude 11'-(4-methoxyphenylamine)-3-(tert-butyldimethylsilanyloxy)vinorelbine: ESI MS m/z 1014 [M+H]$^+$.

Step 2: A solution of 11'-(4-methoxyphenylamino)-3-(tert-butyl-dimethylsilanyloxy)vinorelbine (17 mg, 0.016 mmol) in THF (1.0 mL) was treated with Bu$_4$NF (50 μL of a 1 N solution in THF, 0.050 mmol). After 1.5 h, the reaction appeared complete as indicated by ESI mass spectral analysis. The reaction mixture was diluted with saturated NaHCO$_3$ (10 mL) and extracted with CH$_2$Cl$_2$ (2×10 mL). The combined extracts were dried (Na$_2$SO$_4$), concentrated, and purified by reverse phase chromatography (C18, acetonitrile/water, 0.05% TFA) to provide 11'-(4-methoxyphenylanime)vinorelbine trifluoroacetate (16 mg, 13% yield) as a white powder after lyophilization: $^1$H NMR (500 MHz, CD$_3$OD) δ 9.97 (br s, 1H), 7.33-7.27 (m, 2H), 7.03 (d, J=7 Hz, 2H), 6.91 (d, J=8 Hz, 1H), 6.82 (d, J=8.5 Hz, 2H), 6.63 (s, 1H), 6.42 (s, 1H), 5.94 (dd, J=10.5, 4.0 Hz, 1H), 5.86-5.85 (m, 1H), 5.63 (d, J=9.5 Hz, 1H), 5.32 (s, 1H), 5.76 (d, J=14.5 Hz, 1H), 5.68-5.64 (m, 1H), 4.03 (d, J=16.5 Hz, 1H), 3.97-3.81 (m, 8H), 3.79-3.70 (m, 8H), 3.47-3.44 (m, 1H), 3.20-3.07 (m, 3H), 2.84-2.78 (m, 4H), 2.62-2.57 (m, 1H), 2.37-2.32 (m, 1H), 2.16-2.03 (m, 7H), 1.95-1.91 (m, 1H), 1.68-1.64 (m, 1H), 1.47-1.44 (m, 1H), 1.12 (t, J=7.5 Hz, 3H), 0.76 (t, J=7.5 Hz, 3H); ESI MS m/z 900 [M+H]$^+$.

Example 37

Description of Biological Assays

A. HeLa GI$_{50}$ Determinations

Growth inhibition (GI$_{50}$) values were measured on the human cervical carcinoma cell line, HeLa S-3, which were selected for growth on plastic. The HeLa cell assay was based on the description of Skehan et al., *J. Natl. Cancer Inst.*, 82:1107-12 (1990), which is hereby incorporated by reference in its entirety. HeLa cells were plated at 2×10$^4$ cells/well in 96 well plates. One day later, a control plate was fixed by the addition of TCA to 5%. After five rinses with tap water, the plate was air-dried and stored at 4° C. Test compounds were added to the remaining plates at 10-fold dilutions. Two days later, all plates were fixed as described above. Cells were then stained by the addition of 100 μL per well of 0.4% sulforhodamine B (SRB) in 1% acetic acid for 30 min at 4° C. Wells were then quickly rinsed 5× with 1% acetic acid and allowed to air dry. The SRB was then solubilized by the addition of 100 μL per well of unbuffered 10 mM Tris base. Dye was quantified by measuring absorbance at 490 nm on a Molecular Devices microplate reader. Growth inhibition was calculated according to the following equation: GI=100×(T−T$_0$)/(C−T$_0$), where the optical density (OD) of the test well after 2 days of treatment was T, the OD of the wells in the control plate on day 0 was T$_0$ and C was the OD of untreated wells. Plots of percent growth inhibition versus inhibitor concentration were used to determine the GI$_{50}$.

B. MCF-7 GI$_{50}$ Determinations

Growth inhibition (GI$_{50}$) values were measured on the human breast carcinoma line, MCF-7. MCF-7 cells were plated at 2×10$^4$ cells/well in 96 well plates and grown for 24 hours in drug free media. On day 2, test compounds were added to the plates at 10-fold dilutions. Four days later, cells were fixed by the addition of glutaraldehyde to 0.75%. After 30 min, the fixed cells were extensively rinsed with distilled water and dried at room temperature for one hour. The cells were then stained with a 0.2% crystal violet solution for one hour at room temperature. Unbound stain was removed by ten rinses with tap water and plates were allowed to air dry for 30 min. The crystal violet was then solubilized by the addition of 10% acetic acid for 15 min and quantified by measuring absorbance at 570 nm on a Molecular Devices microplate reader. Growth inhibition was calculated according to the following equation: GI=100×(T/T$_0$), where the optical density (OD) of the test well after 4 days of treatment was T, the OD of the wells in the control plate on day 0 was T$_0$. Plots of percent growth inhibition versus inhibitor concentration were used to determine the GI$_{50}$.

TABLE 3

Growth Inhibition (GI$_{50}$) of HeLa Cells for Compounds of the Current Invention.

| Example | HeLa Cells GI$_{50}$ (nM) | MCF-7 Cells GI$_{50}$ (nM) |
|---|---|---|
| 1 | 5 | 3 |
| 2 | 25 | 7 |
| 3 | 3 | 7 |
| 4 | 400 | 300 |
| 5 | 300 | 600 |
| 6 | 800 | >1000 |
| 7 | 200 | 400 |
| 8 | 40 | 60 |
| 9 | 20 | 30 |
| 10 | 0.3 | 1 |
| 11 | 5 | 20 |
| 12 | 20 | 40 |
| 13 | 20 | 30 |
| 14 | 30 | 50 |
| 15 | 200 | 400 |
| 16 | 300 | 500 |
| 17 | 20 | 300 |
| 18 | 30 | 300 |
| 19 | 300 | >1000 |
| 20 | 40 | 300 |
| 21 | 0.4 | 5 |
| 22 | 40 | 50 |
| 23 | 300 | 300 |
| 24 | 100 | 300 |
| 25 | 1 | 6 |
| 26 | 4 | 20 |
| 27 | 30 | 50 |
| 28 | 300 | >1000 |
| 29 | 70 | 300 |
| 30 | 70 | 300 |
| 31 | 300 | 600 |
| 32 | 300 | 400 |
| 33 | 30 | 50 |
| 34 | 30 | 30 |
| 35 | 300 | 600 |
| 36 | 300 | 400 |

C. NCI Sixty Cell Line Data

The following data in Table 4 summarize the growth inhibition properties of several compounds of the present invention against 60-human transformed cell lines. These data were cooperatively obtained at the National Cancer Institute in their 60-cell line growth inhibition assay according to published procedures (Boyd, M. R., "Anticancer Drug Development Guide," *Preclinical Screening, Clinical Trials, and Approval*; Teicher, B. Ed.; Humana Press; Totowa, N.J., 23-42 (1997), which is hereby incorporated by reference in its entirety).

TABLE 4

In Vitro Growth Inhibition (GI$_{50}$) of NCI Human Transformed Cell Lines of Several Compounds of the Current Invention.

| Cancer Type | Cell Line | 1 GI$_{50}$ (nM) | 2 GI$_{50}$ (nM) |
|---|---|---|---|
| Breast | BT-549 | <10 | — |
| Breast | HS 578T | 679 | 19.2 |
| Breast | MCF7 | <10 | 11.3 |
| Breast | MDA-MB-231/ATCC | <10 | 77.2 |
| Breast | MDA-MB-435 | <10 | 1370 |
| Breast | NCI/ADR-RES | 152 | 5280 |
| Breast | T-47D | — | — |
| CNS | SF-268 | <10 | 78.8 |
| CNS | SF-295 | <10 | 27 |
| CNS | SF-539 | <10 | 37.9 |
| CNS | SNB-19 | — | 62.5 |
| CNS | SNB-75 | 15100 | 40.4 |
| CNS | U251 | <10 | 42.3 |
| Colon | COLO 205 | — | 17.9 |
| Colon | HCC-2998 | — | <10 |
| Colon | HCT-116 | <10 | — |
| Colon | HCT-15 | <10 | 1070 |
| Colon | HT29 | <10 | 10.3 |
| Colon | KM12 | <10 | 92.7 |
| Colon | SW-620 | <10 | 37.8 |
| Leukemia | CCRF-CEM | <10 | 37.9 |
| Leukemia | HL-60(TB) | <10 | 71 |
| Leukemia | K-562 | <10 | 12.4 |
| Leukemia | MOLT-4 | — | 24.1 |
| Leukemia | RPMI-8226 | <10 | 16.7 |
| Leukemia | SR | >100000 | 26.1 |
| Melanoma | LOX IMVI | <10 | 31.3 |
| Melanoma | M14 | <10 | >100000 |
| Melanoma | MALME-3M | 53.6 | 65 |
| Melanoma | SK-MEL-2 | <10 | 1400 |
| Melanoma | SK-MEL-28 | — | 91.4 |
| Melanoma | SK-MEL-5 | — | 18.8 |
| Melanoma | UACC-257 | 5730 | 3430 |
| Melanoma | UACC-62 | <10 | 25.6 |
| Non-Small Cell Lung | A549/ATCC | <10 | 58.6 |
| Non-Small Cell Lung | EKVX | — | 72.6 |
| Non-Small Cell Lung | HOP-62 | <10 | 37 |
| Non-Small Cell Lung | HOP-92 | 1240 | 2250 |
| Non-Small Cell Lung | NCI-H226 | <10 | 83.3 |
| Non-Small Cell Lung | NCI-H23 | <10 | 52.8 |
| Non-Small Cell Lung | NCI-H322M | <10 | — |
| Non-Small Cell Lung | NCI-H460 | <10 | 43.2 |
| Non-Small Cell Lung | NCI-H522 | <10 | <10 |
| Ovarian | IGROV1 | <10 | 32.4 |
| Ovarian | OVCAR-3 | <10 | — |
| Ovarian | OVCAR-4 | — | 264 |
| Ovarian | OVCAR-5 | — | 225 |
| Ovarian | OVCAR-8 | <10 | 51.7 |
| Ovarian | SK-OV-3 | — | 63.3 |
| Prostate | DU-145 | <10 | 25.7 |
| Prostate | PC-3 | <10 | 57.3 |
| Renal | 786-0 | <10 | — |
| Renal | A498 | <10 | — |
| Renal | ACHN | 3230 | 1430 |
| Renal | CAKI-1 | <10 | — |
| Renal | RXF 393 | 10300 | 60.5 |
| Renal | SN12C | <10 | 70.8 |
| Renal | TK-10 | <10 | 298 |
| Renal | UO-31 | <10 | 674 |
| Renal | RPMI-8226 | <10 | 16.7 |

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A compound of the following chemical formula:

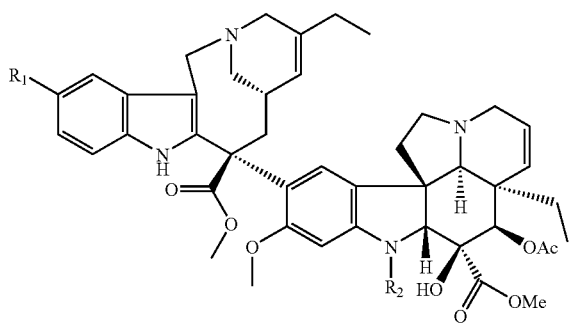

where:

$R_1$ is
  alkenyl;
  alkynyl;
  CN;
  $SR_5$; or
  $CF_3$;

$R_2$ = alkyl or CH(O);

$R_5$ = hydrogen, alkyl, alkenyl, alkynyl, aryl, or heterocyclyl;

or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

2. A compound of the following chemical formula:

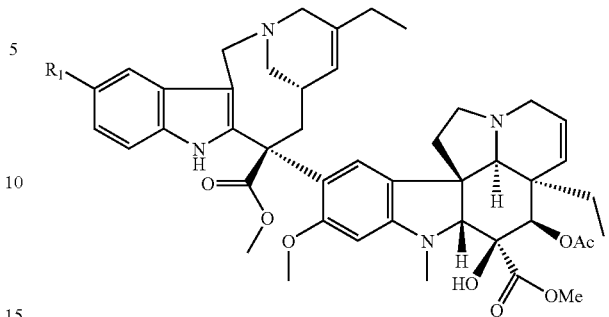

where:

$R_1 = SR_5$;

$R_5$ = hydrogen, alkyl, alkenyl, alkynyl, aryl, or heterocyclyl;

or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted.

3. A compound of the following chemical formula:

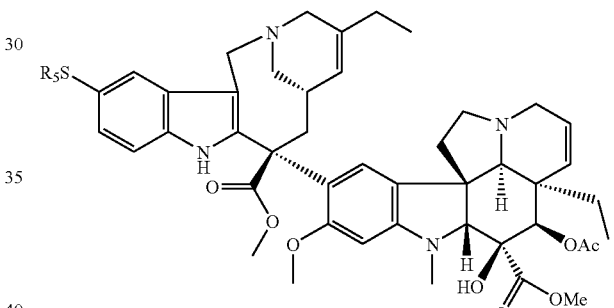

where:

$R_5$ = alkyl;

or a pharmaceutically acceptable salt thereof, wherein the alkyl group may be branched, straight, unsubstituted, and/or substituted.

* * * * *